United States Patent
Yu et al.

(10) Patent No.: US 8,722,416 B2
(45) Date of Patent: May 13, 2014

(54) INTEGRATED ON-LINE TWO-DIMENSIONAL METHOD AND DEVICE FOR SYNCHRONED ANALYTICAL TEMPERATURE RISING ELUTION FRACTIONATION AND GEL PERMEATION CHROMATOGRAPHY

(75) Inventors: Youlu Yu, Bartlesville, OK (US); Chung C. Tso, Bartlesville, OK (US); Paul J. DesLauriers, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 1344 days.

(21) Appl. No.: 11/439,646

(22) Filed: May 24, 2006

(65) Prior Publication Data

US 2006/0266708 A1 Nov. 30, 2006

Related U.S. Application Data

(60) Provisional application No. 60/684,044, filed on May 24, 2005.

(51) Int. Cl.
*B01D 15/08* (2006.01)
(52) U.S. Cl.
USPC ............ 436/85; 436/161; 436/178; 422/68.1; 422/70; 422/527; 422/535; 210/635; 210/656; 210/679
(58) Field of Classification Search
USPC ............ 436/85, 161, 178; 210/635, 656, 679; 422/68.1, 70, 527, 535, 85
See application file for complete search history.

(56) References Cited

U.S. PATENT DOCUMENTS

| | | | |
|---|---|---|---|
| 4,798,081 | A | 1/1989 | Hazlitt et al. |
| 5,089,321 | A | 2/1992 | Chum et al. |
| 6,114,486 | A | 9/2000 | Rowland et al. |
| 6,534,612 | B1 | 3/2003 | Lai et al. |
| 7,985,593 | B2 * | 7/2011 | Gillespie et al. ............. 436/161 |
| 2006/0054543 | A1 * | 3/2006 | Petro et al. ................. 210/198.2 |

FOREIGN PATENT DOCUMENTS

| | | | |
|---|---|---|---|
| EP | 1 095 874 A2 | | 5/2001 |
| WO | WO2006/081116 | * | 8/2006 |
| WO | WO 2006/081116 A1 | | 8/2006 |

OTHER PUBLICATIONS

Wilkes, Garth D., "Structure-Property Behavior of Polymeric Systems," Poly Sci & Eng., Macromolecular Associates, Inc., vol. 15, 8 pgs.
Shugar, Gershon J., et al., "The Chemist's Ready Reference Handbook," McGraw-Hill Publishing Company, 1989, 7 pgs.

(Continued)

Primary Examiner — Krishnan S Menon
Assistant Examiner — Dwan A Gerido
(74) Attorney, Agent, or Firm — Conley Rose, P.C.; Rodney B. Carroll; Cheryl L. Huseman

(57) ABSTRACT

An analytical method comprising performing a first fractionation of a polymer sample based on differences in crystallizability to provide a first set of sample fractions, performing a first analysis on the first set of sample fractions, performing a second fractionation of the first set of sample fractions to produce a second set of sample fractions, performing a second analysis on the second set of sample fractions, and synchronizing the first fractionation and second fractionation to provide about concurrent analysis of the polymer sample.

26 Claims, 20 Drawing Sheets

(56) References Cited

OTHER PUBLICATIONS

Wang, Wen-Jun, et al., "Temperature rising elution fractionation and characterization of ethylene/octene-1 copolymers synthesized with constrained geometry catalyst," Macromolecular Chemistry and Physics, vol. 200, No. 9, 1999, 1 pg., http://www3.interscience.wiley.com/cgi-bin/abstract/63002918/ABSTRACT.

Zhang, Mingqian, et al., "Characterization of commercial linear low-density polyethylene by TREF-DSC and TREF-SEC cross-fractionation," Journal of Applied Polymer Science, vol. 75, No. 7, 2000, 1 pg., http://www3.interscience.wiley.com/cgi-bin/abstract/69500382/ABSTRACT.

Boborodea, Adrian G., et al., "An Improved Analytical Temperature-Rising Elution Fractionation System for Automated Analysis of Polyethylenes," LCGC North America, Advanstar Communications, vol. 22, No. 1, Jan. 2004, 4 pgs.

Yua W. W., "New approaches using MW-sensitive detectors in GPC-TREF for polyolefin characterization", Polymer, vol. 42, No. 21, Oct. 2001, pp. 8947-8958.

Abiru T., "Microstructural characterization of propylene-butene-1 copolymer using temperature rising elution fractionation", Journal of Applied Science, vol. 68, No. 9, May 31, 1998, pp. 1493-1501.

Morgan R.L., "Liquid-liquid phase separation ternary blends of linear polyethylene with two ethylene-butene copolymers", Polymer, vol. 38, No. 8, Apr. 1997, pp. 1903-1909.

Yua W.W., "A trisec and 3D-TREF approach to polymer blend design", TAAPI Proceedings Polymers, No. 2, Aug. 31, 2000, pp. 699-707.

Seikou Nakano, "Development of automatic cross fractionation: combination of crystallizability fractionation and molecular weight fractionation", Journal of Applied Polymer Science, vol. 26, No. 12, Dec. 1981, pp. 4217-4231.

International Search Report and Written Opinion, PCT/US06/019933, Sep. 27, 2006, 14 pgs.

\* cited by examiner

OVERVIEW OF aTREF -rGPC

POSITION IV
INJECTION

POSITION III
FILLING THE LOOP

US 8,722,416 B2

INTEGRATED ON-LINE TWO-DIMENSIONAL METHOD AND DEVICE FOR SYNCHRONED ANALYTICAL TEMPERATURE RISING ELUTION FRACTIONATION AND GEL PERMEATION CHROMATOGRAPHY

CROSS-REFERENCE TO RELATED APPLICATIONS

This application claims priority to U.S. Provisional Patent Application Ser. No. 60/684,044 filed on May 24, 2005, which is hereby incorporated by reference in its entirety.

STATEMENT REGARDING FEDERALLY SPONSORED RESEARCH OR DEVELOPMENT

Not applicable.

FIELD OF THE INVENTION

The present invention relates to polymer characterization and more particularly to the simultaneous analysis of chemical composition distribution and molecular weight distribution of a polymer sample using a combination of analytical temperature rising elution fractionation (aTREF) and rapid gel permeation chromatography (rGPC).

BACKGROUND OF THE INVENTION

Knowledge of polymer microstructure is critical to understanding the potential utility of a polymer blend. Analysis of polymer microstructure has typically relied on analytical techniques capable of providing data on the chemical composition, molecular weight, and molecular weight distribution (MW/MWD) of a polymer sample.

Temperature rising elution fractionation (TREF) separates polymeric molecules based on their crystallizability. TREF separation is a two-step process in which a dissolved polymer sample is deposited onto a column filled with inert packing material by programmed cooling of the column. The sample is then redissolved into the flowing solvent or mobile phase by raising the temperature of the column slowly while flushing the column with solvent. The temperature at which the polymer fractions elute off the column is primarily a function of the extent of short-chain branching (SCB) within the sample, molecular weights, and the thermal history the polymer has experienced. TREF analysis can be carried out on two scales depending on the amount of sample to be fractionated. Typically, a polymer sample is analyzed using preparation scale or pTREF in order to generate enough sample after fractionation to carry out additional characterization of polymer microstructure. Analytical scale TREF or aTREF is considered an improvement over pTREF because the technique requires less polymer sample and the amount of eluting polymer sample can be monitored using an on-line detector. However, aTREF analysis alone provides limited information on polymer microstructure. One limitation of aTREF analysis is that aTREF does not differentiate between polymers possessing similar melting points/elution temperatures, yet dramatically different molecular weights, molecular weight distributions, SCB distribution across the molecular weight distribution and long-chain branching distribution across the molecular weight distribution. Furthermore, information obtained from pTREF is not necessarily applicable to aTREF because there are differences in thermal histories experienced by the polymer in the two processes.

Gel permeation chromatography (GPC), also known as size-exclusion chromatography (SEC), is a useful technique for characterizing the molecular weight or molecular weight distribution (MW/MWD) of a polymer sample. Separation is accomplished by injecting the sample into a column packed with a porous packing material such as a crosslinked poly (styrene-co-divinylbenzene) gel. Without wishing to be limited by theory, GPC separation is based on differences in hydrodynamic volume. Molecules too large to enter the small pores in the packing material elute from the column first while those that can enter the small pores require a longer time or larger elution volume to elute from the column.

Routine characterization of polymer microstructure requires information from both TREF and GPC analysis. A major impediment to utilizing both TREF and GPC for polymer microstructure characterization is the need to carry out offline analysis of polymer sample fractions isolated from TREF prior to subjecting the polymer sample fractions to GPC analysis. This offline processing of the polymer sample first by pTREF fractionation, collecting the fractionated samples and then by GPC is a very tedious one. To finish a complete pTREF run with offline GPC analysis for a polymer sample usually requires two to three months, depending on the number of individual thermal cutoffs analyzed. A need therefore exists for a quick and reliable two-dimensional technique that concurrently determines the chemical composition and MW/MWD for a given temperature slice.

SUMMARY OF THE INVENTION

Disclosed herein is an analytical method comprising fractionating a polymer sample based on differences in crystallizability to obtain sample fractions; and characterizing the polymer sample by concurrently determining a composition and a molecular weight distribution of the sample fractions. The fractionation may be performed across a temperature gradient. The molecular weight distribution may be determined via size exclusion chromatography. The size exclusion chromatography may be rapid gel permeation chromatography. The method may further comprise heating the sample fractions prior to the rapid gel permeation chromatography. The method may further comprise implementing a valve scheme for completing concurrent determination of the composition and molecular weight distribution. The method may further comprise computer control of the concurrent determination of the composition and molecular weight distribution. The concurrent determination of the composition and molecular weight distribution may comprise operation of an integrated device having the synchronized capabilities of analytical temperature rising elution fractionation (aTREF) and rapid gel permeation chromatography (rGPC). The concurrent determination of the composition and molecular weight distribution may be an online and/or real-time process that may be graphically represented. The graphical representation may simultaneously present data on polymer composition, molecular weight, and molecular weight distribution.

Further disclosed herein is a device for characterizing a polymer sample comprising a first column for fractionating a polymer sample via temperature gradient (TGC); a polymer composition detection device in fluid communication with the first column to receive a first portion of the fractions of the polymer sample; at least a second column in fluid communication with the first column to receive a second portion of the fractions of the polymer sample, wherein the second column further separates polymers from the fraction; a second detection device in fluid communication with the second column to receive the polymers separated from the fraction and characterize a physical property of same; and a computer that synchronizes operation of the TGC and the at least one second column for concurrent determination of the chemical and physical properties of the polymer sample. The device may further comprise a valve scheme that regulates conveyance of polymer samples into the first column. The second column may separate polymers from the fraction based on molecular size and/or chemical composition. The device may comprise the capabilities of an integrated and synchronized aTREF apparatus and an rGPC, and in particular wherein the first column is part of the aTREF apparatus (e.g., a temperature gradient column) and the second column is part of the rGPC apparatus (e.g., a molecular weight column). The valve scheme may comprise multi-port valves.

Further disclosed is an analytical method comprising introducing a sample to an analytical device having synchronized aTREF and rGPC elements; operating the analytical device; and determining the concentration, molecular weight, and molecular weight distribution of a polymer sample in less than about 8 hours.

Further disclosed is an analytical method comprising fractionating a polymer sample based on differences in crystallizability to obtain sample fractions; detecting any composition of the sample fractions; separating any polymers in the sample fractions based on differences in molecular weight; detecting any molecular weight distribution of polymers in the sample fractions; and characterizing the polymer sample, wherein the composition and molecular weight distribution are determined concurrently.

DESCRIPTION OF THE DRAWINGS

The invention, together with further advantages thereof, may best be understood by reference to the following description taken in conjunction with the accompanying drawings in which.

DETAILED DESCRIPTION OF THE PREFERRED EMBODIMENTS

Figure 1:
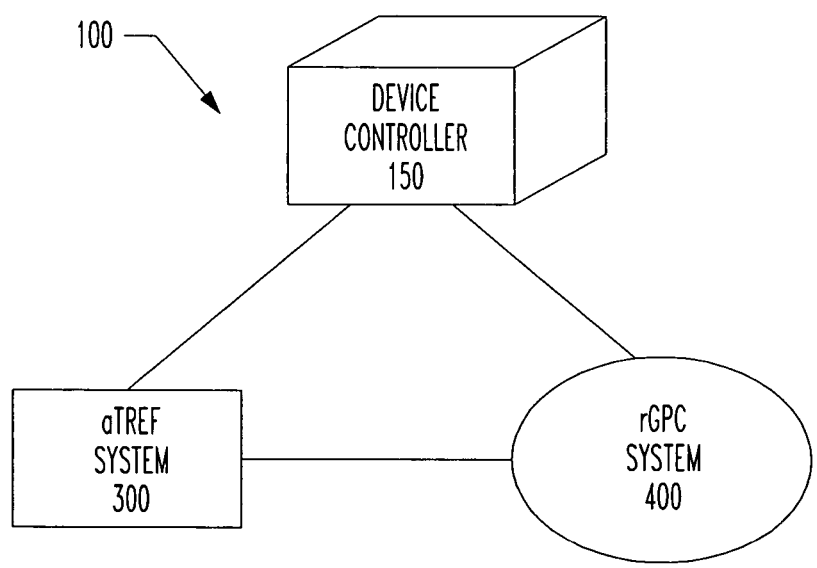
FIG. 1 is a schematic representation of an aTREF-rGPC device.

Referring to FIG. 1, a device 100 comprises a system having the capabilities of aTREF ("aTREF system") 300 coupled with a system having the capabilities of rGPC ("rGPC system") 400. As will be understood by one skilled in the art, the term rapid GPC (rGPC) collectively refers to rGPC, fast GPC (fGPC), high throughput GPC (htGPC), rapid SEC (rSEC), fast SEC (fSEC), and high throughput SEC (htSEC) and further refers to GPC or SEC carried out in a shorter time frame than associated with conventional GPC or SEC methods. The term rGPC is used throughout this disclosure, and it is to be understood the term is representative of all GPC and/or SEC methods that can be conducted in a time frame compatible with the disclosed devices and methodologies. The device ("aTREF-rGPC device") 100 is controlled, including synchronization of the aTREF system 300 and rGPC system 400, by a device controller 150. The systems 300, 400 and controller 150 may accomplish the synchronized, online analysis of chemical samples, and in particular polymer samples. Online refers to the electronic coupling (e.g., networking), operation, and communication of systems 300, 400 via controller 150, which may be implemented via one or more computers, microprocessors, controllers, and the like. In an embodiment, the sample is any polymeric material whose solubility changes as a function of solvent temperature. In an embodiment of FIG. 1, the aTREF system 300 is coupled to the rGPC system 400, and the device controller 150 may control the two systems such that the output from the two systems is synchronized in real-time. In embodiments, the aTREF system 300 and rGPC system 400 may be coupled for concurrent, online operation. In some embodiments, the aTREF system 300 and rGPC system 400 are part of an integrated, linked device combined within a common housing or assembly. For example, the aTREF unit and rGPC unit may be connected through a hot transfer line whose temperature is regulated to match that of the rGPC column/detector compartment.

In various embodiments, an aTREF-rGPC device is a device for characterizing a polymer sample. Such a device may comprise: a column packed with inert hard-spheres that fractionate polymers via a temperature gradient for example by temperature rising elution fractionation ("TREF column" or "TC"); a polymer composition detection device; a column for separating polymers according to their size (or hydrodynamic volume) ("molecular weight column" or "MWC"); a polymer concentration detection device; a valve scheme that regulates conveyance of sample fractions to the MWC; and a computer that performs synchronized operation of the TC and MWC for concurrent determination of the composition, molecular weight, and molecular weight distribution of the polymer sample.

Herein the detection of polymer composition may include detection of polymer primary structure, secondary structure, tertiary structure or combinations thereof. As will be understood by one skilled in the art, polymer primary structure refers to how a single polymer chain is put together. For example, the primary structure may refer to the chemical composition of the polymer and the types of branching in the polymer. Secondary structure refers to the three dimensional conformation of the polymer and the polymer chain configuration. Examples of secondary structure include conformations such as random coil, folded chain and spiraled chain or helix. Polymer chain configuration cannot be changed without breaking and reforming the primary (covalent) bonds. Tertiary structure and higher refers to the interactions of one polymer chain with another polymer chain. Examples of tertiary structure include, for example, over-spiralling, also known as the super helix. Included in the tertiary structures is the polymer morphology.

In an embodiment, fractionating via a TC is accomplished via TREF. A device for characterizing a polymer sample may comprise the capabilities of an aTREF system in order to determine the composition of polymers in the sample. In an embodiment, a column for separating polymers may separate via size exclusion chromatography, such as via rGPC. Further, a device for characterizing a polymer sample may comprise the capabilities of a rGPC system in order to determine the molecular weight distribution within a fraction of polymers. In some embodiments, a fractionation based on methods other than the combination of aTREF and rGPC may be carried out. For example, the aTREF may be coupled to a device that separates a polymeric material based on chemical composition such as a hydrophobic interaction column, an ion exchange column, a high performance liquid chromatography (HPLC) column, or combinations thereof. In an embodiment, the aTREF column may be coupled to any column capable of carrying out fractionation of a polymeric material eluting from an aTREF column. Such devices would be subject to the design and controls described herein.

In embodiments, an aTREF-rGPC device integrates and synchronizes the capabilities of an aTREF system and a rGPC system. In some embodiments such a device comprises a valve scheme, such as a valve scheme including a six-port valve (SPIV), which regulates conveyance of fractions of polymers to a MWC.

Figure 2:
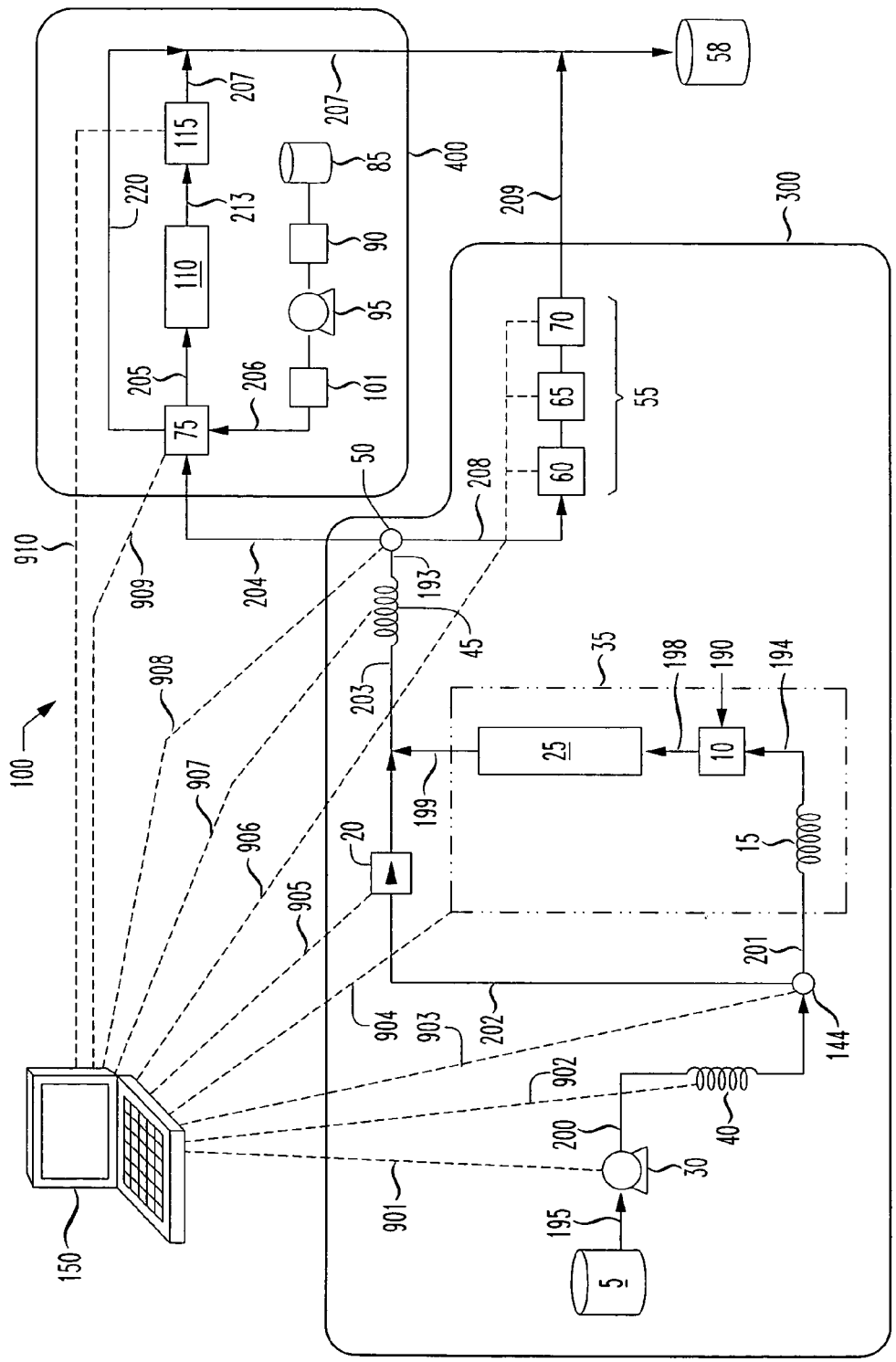
FIG. 2 is a flow diagram representing an embodiment of the components of an aTREF-rGPC device.

A device and method for characterizing a polymer sample may be illustrated by reference to the embodiment of FIG. 2. The aTREF-rGPC device 100 of FIG. 2 comprises the elements disclosed in FIG. 1: the controller 150, aTREF system 300, and rGPC system 400. In addition, FIG. 2 illustrates some embodiments of the components and functionality in each of the systems 300 and 400. A polymer solution may be introduced to the aTREF-rGPC device 100 via line 190 at sample injection device 10. Sample injection device 10 may be housed in a heating oven 35, which may also house temperature equilibrium coil 15 and aTREF column 25. Line 190 may represent any method employed by one skilled in the art to deliver a polymer sample to an aTREF system. The controller 150 as indicated by connection 904 may operate the heating oven 35, and components housed within the heating oven 35.

The temperature of the heating oven 35, and the column 25, sample injection device 10, and temperature equilibrium coil 15 housed within the heating oven 35, may be manually operated or coupled to and operated by the device controller 150 via connection 904. In an embodiment, the heating oven 35 and the components it houses may be cooled and heated in a temperature range from about 25° C. to about 250° C. at a rate from about 0.1° C./min to 20° C./min.

In the present embodiment, a suitable solvent originating from solvent reservoir 5 may carry the polymer sample from the sample injection device 10 via line 198 to the aTREF column 25. In an alternative embodiment, an appropriately solubilized polymer sample may be introduced directly into the aTREF column 25. A suitable solvent is one employed by those skilled in the art, which generally remains inert and liquid under the process conditions to be described. Examples of suitable solvents for polyolefins include but are not limited to 1,2,4-trichlorobenzene, o-dichlorobenzene, 1,3,5-trimethylbenzene, 1-chloronaphthalene, and xylene. In an embodiment, the solvent is any material capable of dissolving the polymeric sample (e.g., a semicrystalline polymer) and that is chemically compatible with the sample and aTREF-rGPC device.

Solvent originating from solvent reservoir 5 may be conveyed via line 195 and line 200 by pump 30. Solvent pre-heater 40 may heat the solvent as it passes along line 200 towards the heating oven 35. Solvent pre-heater 40 and temperature equilibrium coil 15 may suitably set the temperature of the solvent feed to the sample injection device 10 and aTREF column 25. At valve 144, the solvent may be routed to the heating oven 35 where it reaches the aTREF column 25 via a flow path comprising line 201, temperature equilibrium coil 15, line 194, sample injection device 10, and line 198. Alternatively, at valve 144 the solvent may be routed to bypass the aTREF column 25 via line 202. The pump 30, solvent pre-heater 40, and valve 144 may each be manually operated or operated by the controller 150 via connections 901, 902, and 903, respectively. Check valve 20 regulates the flow of solvent from line 202 to line 203, and in particular may prevent backflow resulting from conveyances from line 199 to line 203. Check valve 20 may be a static (i.e., "dumb") device requiring no operation or may be manually operated or may be regulated by the controller 150, as indicated by connection 905.

Figure 3:
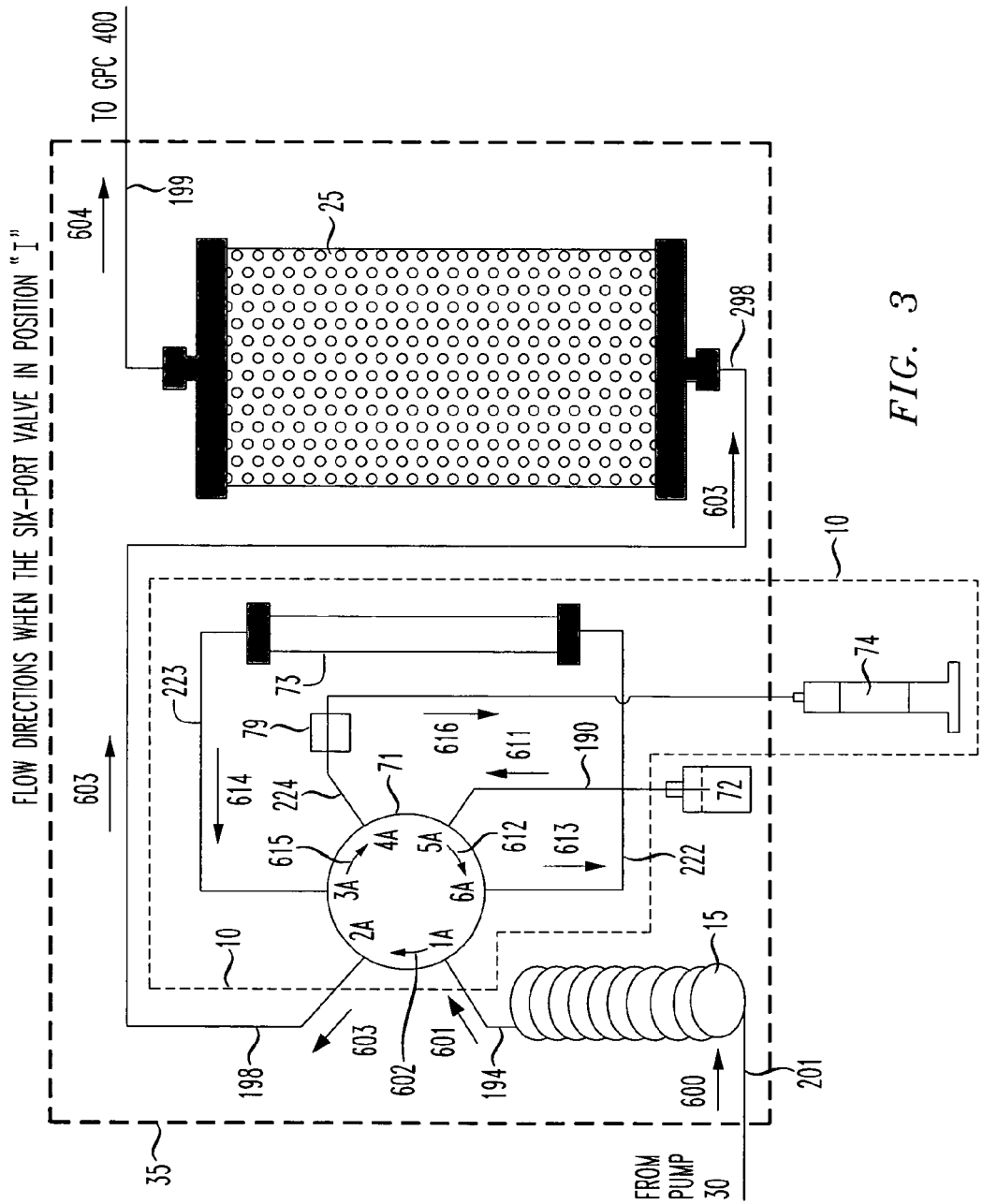
FIG. 3 is a flow diagram of a multi-port injection valve in position I.

FIG. 3 provides a more detailed illustration of an embodiment of a heating oven 35, which is shown in FIG. 2 as a part of the aTREF system 300 in the aTREF-rGPC device 100. As in FIGS. 2 and 3, the heating oven 35 comprises an aTREF column 25, a temperature equilibrium coil 15, and a sample injection device 10. In the embodiment of FIG. 3, the sample injection device 10 comprises a multi-port valve 71, sample tube 73 and syringe 74. In an embodiment shown in the Figures, the multi-port valve 71 is a six-port valve having ports 1-6A, which is referred to herein as SPIV 71. It should be understood that other multi-port configurations may be used having a suitable number of ports for a desired operational configuration. For example, duplicate or multiple components (which may be the same or different) within sample device 10 such as solvents, sample tubes, syringes, polymer sample containers, and outputs to aTREF column 25, may be placed in fluid communication via one or more appropriately configured multi-port valves. In an embodiment, one or more multi-port valves is in fluid communication with one or more additional multi-port valves.

The embodiment of FIG. 3 further comprises a polymer sample container 72, which provides polymer samples to the polymer sample injector 10 via line 190. Solvent is fed via line 201 to the temperature equilibrium coil 15, which further passes solvent to the sample injection device 10 via line 194. Conveyance from the sample injection device 10 to the aTREF column 25 is via line 198, and conveyance on the downstream side (e.g., overhead) of the column 25 is via line 199. Line 190 of FIG. 2 corresponds to line 190 exiting the polymer sample container 72 of FIG. 3, which carries polymer samples to the sample injection device 10. Direction arrows 600 through 604, and 611 through 616 indicate the flow directions in the lines of FIG. 3 when SPIV 71 is in a first or load position ("position I").

The configuration of the SPIV 71 illustrated in the embodiment of FIG. 3 loads a polymer sample into the polymer sample injector 10. When the SPIV 71 is in position I, ports 1A, 3A and 5A are connected with ports 2A, 4A, and 6A, respectively. Solvent flow from pump 30 is conveyed downstream, indicated by direction arrow 600, via line 201 to temperature equilibrium coil 15. Solvent exiting the coil 15 via line 194, indicated by direction arrow 601, then flows through the SPIV 71 at ports 1A and 2A, indicated by direction arrow 602, before exiting the SPIV 71 and flowing downstream via line 198, indicated by direction arrow 603, to the aTREF column 25.

In the embodiment of FIG. 3, the polymer sample originates in the polymer sample container 72 so that it can be drawn to fill the sample tube 73 using syringe 74. Drawing on the syringe 74 moves the polymer solution from the polymer sample container 72 to port 5A of the SPIV 71 via line 190, as indicated by direction arrow 611. Port 5A is connected to port 6A as indicated by direction arrow 612, and the polymer sample may thus be conveyed via line 222 from the SPIV 71 to the sample tube 73, as indicated by direction arrow 613. Drawing on the barrel of syringe 74 may further move polymer sample through the sample tube 73 and via line 223 towards SPIV port 3A as indicated by direction arrow 614. The polymer sample (or other liquid e.g., pure solvent, in front of the same) flows from port 3A to port 4A as indicated by direction arrow 615. Another hollow tube termed a "knockout pot" 79 may be inserted between port 4A and syringe 74. The knockout pot 79 may function to prevent polymer solution from being drawn into the syringe barrel 74 where the sample could precipitate at ambient temperature and cause the line to clog and/or damage the syringe 74. In an embodiment, the knockout pot 79 is a hollow stainless steel pot whose volume when added to the volume of the sample tube 73 is no less than the volume of the syringe 74. In an alternative embodiment, a polymer sample is inserted directly into the sample tube 73. In yet another embodiment, a pre-loaded sample tube is placed in the solvent flow path to aTREF column 25. An example of a sample tube 73 is a hollow stainless steel tube with fritted caps at both ends connected inline having a capacity from about 1 milliliter to about 100 milliliters.

Thus, the SPIV set in position I permits loading of a polymer sample into the sample tube 73. Meanwhile, solvent may flow as needed via operation of pump 30 directly to the aTREF column 25 through line 200, line 201, line 194, port 1A, port 2A, and line 198, and consequently bypass any polymer in the flow loop comprising the sample tube 73.

Figure 4:
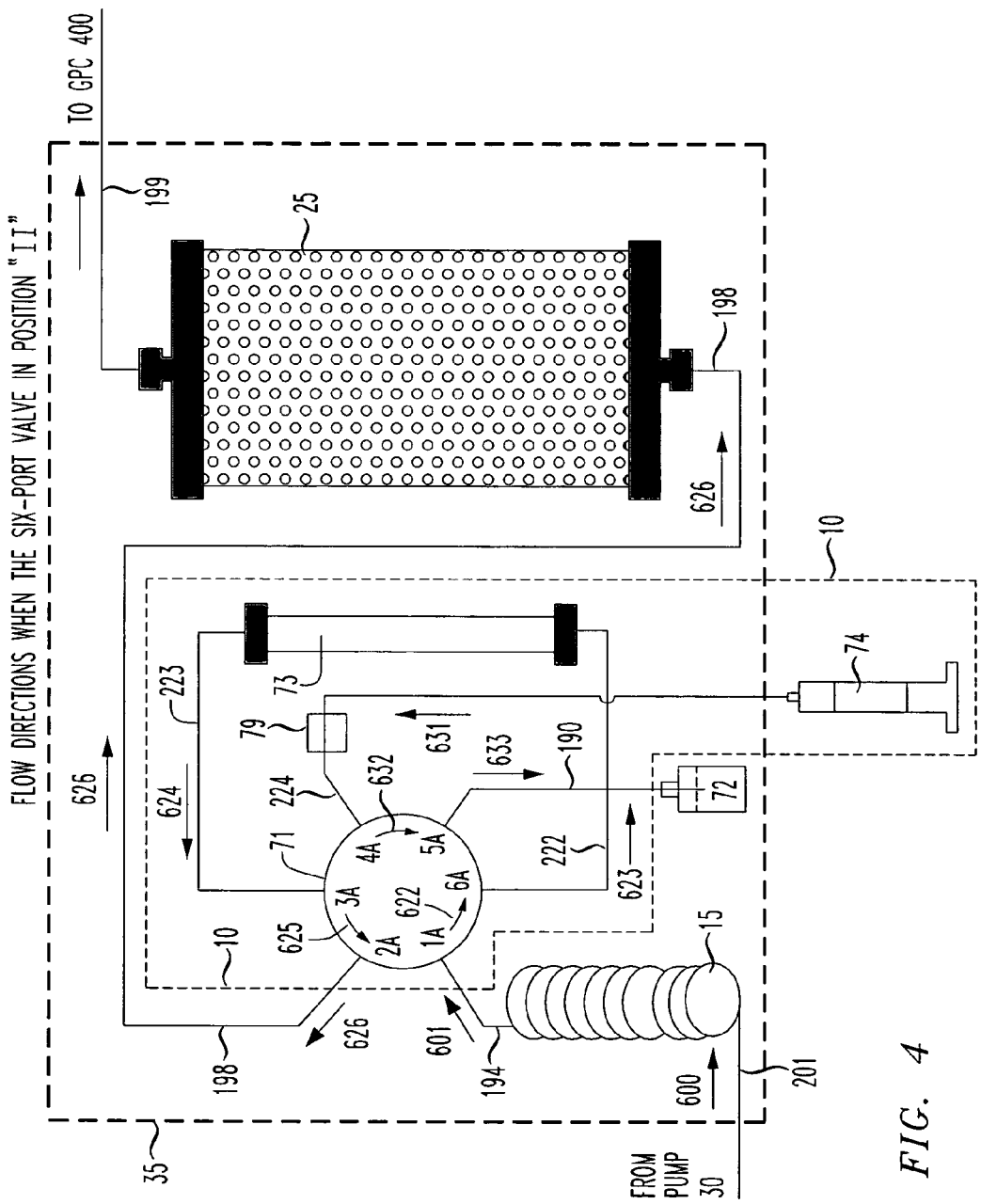
FIG. 4 is a flow diagram of a multi-port injection valve in position II.

FIG. 4 illustrates aTREF-rGPC device elements identical to those shown in FIG. 3, but with modified flow paths. Whereas the embodiment of FIG. 3, i.e.—position I, permits loading of a polymer sample into the sample tube 73, the configuration illustrated by the embodiment of FIG. 4 ("position II") injects polymer sample from the loaded sample tube 73 into the aTREF column 25. Thus, with SPIV 71 in position I, a polymer sample may be loaded into the sample tube 73, and following loading the SPIV 71 may be switched to position II to complete injection of the sample into the aTREF column 25. SPIV 71 may be manually controlled, or coupled to and controlled by the device controller 150.

In the embodiment of FIG. 4, SPIV 71 position II has ports 1A, 3A, and 4A connected to ports 6A, 2A, and 5A, respectively. Solvent flows from the temperature equilibrium coil 15 via line 194 into port 1A as indicated by direction arrow 601. The SPIV 71 then directs the solvent to port 6A as indicated by direction arrow 622, and on to the sample tube 73 via line 222 as indicated by arrow 623. The polymer sample in sample tube 73 is conveyed downstream by the solvent, see direction arrow 624, from the sample tube 73 via line 223 into the SPIV 71 at port 3A. The solvent further conveys the polymer sample through the SPIV 71 to port 2A as indicated by direction arrow 625, and then via line 198 to the aTREF column 25 according to direction arrow 626.

Additionally, in position II the syringe 74 can be used to push polymer sample back into the sample container 72, thus clearing the knock-out pot 79, line 224, port 4A, port 5A, and line 190 as indicated by direction arrows 631, 632, and 633. Alternatively, syringe 74 may flush or clean the lines with another liquid (e.g., fresh solvent), for example by using a substitute syringe loaded with a flushing liquid or pre-charging with a flushing liquid prior to drawing the polymer sample from sample container 72 in position I. The transitioning of the SPIV 71 between position I and position II, and the resultant loading and injecting of the polymer sample, may be manually controlled, or coupled to and controlled by the device controller 150.

In embodiments, a column for fractionating a polymer sample via temperature gradient ("TGC") as provided herein, such as an aTREF column, may be about 4-30 inches (101-762 mm) in length with an internal diameter of about 0.5-3.0 inches (12-77 mm). Such a column may be packed with an inert thermostable packing material having a loading capacity in the range of about 1 to about 100 ml. An example of a suitable packing material includes, but is not limited to, 80-mesh glass beads or sand.

Referring again to the embodiment of FIG. 2, polymer sample loaded into the aTREF column 25 may then be cooled to allow crystallization of the polymer sample onto the packing material in the column. A programmed temperature gradient allows for elution of the polymer sample fractions (PSFs) based on crystallizability into the aTREF mobile phase. PSFs eluting from the aTREF column 25 into line 199 are conveyed via line 203 to heating device 45. Heating device 45 may be a heating coil that is immersed in an oil bath, alternatively the heating coil may be controlled by a programmable heating device. The heating device 45 may be employed for maintaining the PSFs in the aTREF mobile phase to a temperature suitable for rGPC. In an alternative embodiment, heating device 45 may be manually controlled or controlled by the device controller 150 as indicated by connection 907. In an embodiment, line 203 may be encased or constructed of a material capable of good thermal conduction such as copper. A temperature regulator may then regulate the temperature of line 203 either manually or through the use of the device controller 150.

In an embodiment, the PSFs flow downstream from the heating coil 45 into a valve 50 that may split a PSF and direct one portion into line 208 that feeds a detection system 55, while a second portion of the PSF is directed into line 204 that conveys the PSF to an rGPC system 400. Alternatively, valve 50 may allow for flow of the entire PSF downstream through line 208 to detection system 55. And alternatively, valve 50 may allow for flow of the entire PSF downstream via line 204 to rGPC system 400. In some embodiments, the detection system 55 is an element of an aTREF system 300. In an embodiment, valve 50 may be manually controlled or coupled to and controlled by the device controller 150 via connection 908.

In an embodiment, PSFs entering line 208 may be subject to analysis by a detection system 55 before exiting via line 209 and being collected in a waste reservoir 58. In embodiments, the chemical composition of PSFs is analyzed by a spectrometer. Such a spectrometer may measure in the infrared range (IR). In some embodiments, the chemical compositions of PSFs are analyzed by a photometer. Such a photometer may be a low angle light scattering photometer or a multiangle light scattering photometer. In some embodiments, the chemical compositions of PSFs are analyzed by viscosity measurements. The chemical composition of PSFs may be analyzed by any combination of spectrometer, photometer and viscosity detector.

Detection system 55 may be a Fourier transform infrared detector (FTIR) 60, a multiangle light scattering detector (MALS) 65, a viscometer (VISC) 70, or any combination thereof. An example of a suitable infrared detector 60 is the FT-IR Spectrum 2000 commercially available from Perkin-Elmer. An example of a suitable viscometer 70 is the Viscotek 150R viscometer commercially available from Viscotek. An example of a suitable multiangle light scattering detector 65 is the Wyatt Dawn EOS Multiangle Light Scattering detector commercially available from Wyatt Technology Corporation. Suitable FTIR, MALS and VISC are those that would be employed by one skilled in the art. In an embodiment, detection system 55 may be manually controlled or coupled to and controlled by the device controller 150, as shown by connection 906.

The rGPC system 400 of the aTREF-rGPC device 100 shown in the embodiment of FIG. 2 comprises a SPIV 75, MWC 110 (also known as a rGPC column), and a polymer concentration detection device 115. Similar to the SPIV 71 in the sample injector 10 of the aTREF system 300 as shown in FIG. 3 and FIG. 4, the SPIV 75 of the rGPC system 400 regulates injections of the PSFs into the MWC 110. Also in the rGPC system 400 of FIG. 2, line 206 supplies solvent to the SPIV 75. Solvent (e.g., rGPC solvent) is contained in a solvent reservoir 85 and may be pretreated and/or heated. For example, the solvent may pass through a degasser 90 before being transferred by pump 95 through an in-line filter 101 and on to the SPIV 75. Solvent reservoir 85 may be the same as or different than solvent reservoir 5, and in an embodiment, a common reservoir is used.

Figure 5B:
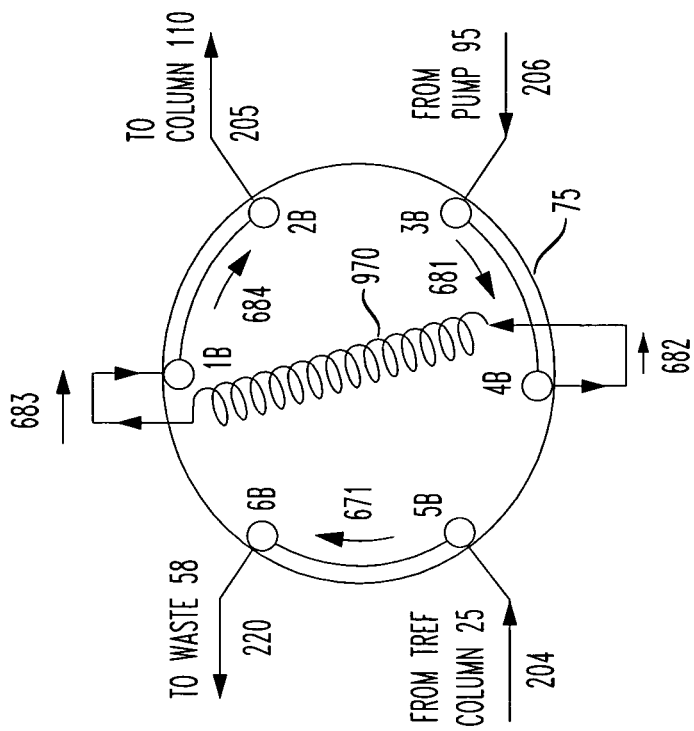
FIGS. 5A and 5B represent an exploded view of a multi-port injection valve.
Figure 5A:
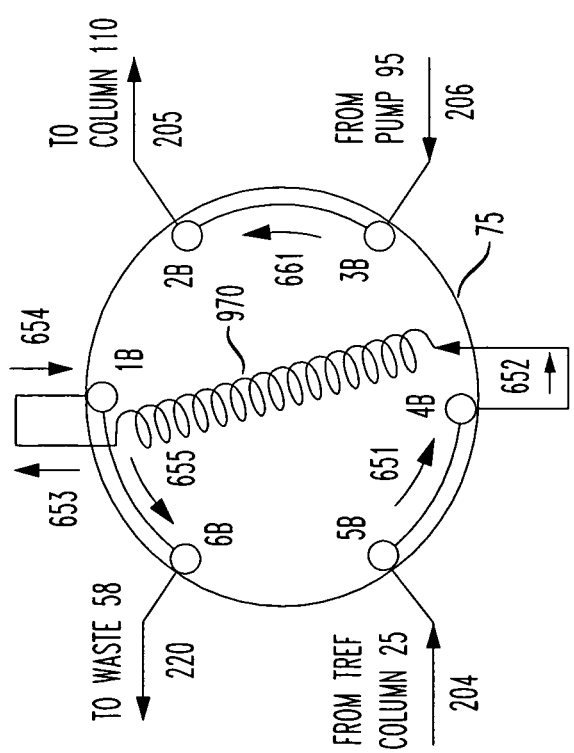

FIG. 5 is an exploded view of the SPIV 75 that is a component of the rGPC system 400 of FIG. 2. In the embodiment of FIG. 5A, position III directs the flow of PSFs from the aTREF system 300 in line 204 through the SPIV 75. Ports 5B and 1B are connected to ports 4B and 6B, respectively. PSFs in line 204 enter the SPIV 75 at port 5B and flow as indicated by direction arrow 651 through port 4B. Likewise, from port 4B the PSFs flow as indicated by direction arrows 652, 653, 654, and 655 through ports 1B and 6B to line 220 and on to waste reservoir 58. Thus, the SPIV 75 may be set in position III in order to load PSFs into the SPIV 75 (more specifically load into injector loop 970) for further injection into the MWC 110, as shown in FIG. 2.

While the SPIV 75 is in position III, solvent pumped from solvent reservoir 85 by pump 95 may bypass the PSFs by flowing in line 206 to the SPIV 75 at ports 3B and 2B, as indicated by direction arrow 661, and on to the MWC 110 via line 205. Selective operation of pump 95 allows for the pumping of solvent to MWC 110 as needed, for example to flush the column. After loading the PSFs in the injector loop 970 in position III, the SPIV 75 may be switched to position IV as indicated in FIG. 5B.

In position IV, ports 3B and 1B of SPIV 75 are connected to ports 4B and 2B, respectively. Solvent from pump 95 in line 206 enters port 3B and flows to port 4B and the injector loop 970 as indicated by direction arrows 681 and 682. In position IV, the solvent conveys PSFs (loaded while the SPIV 75 is in position III) from the injector loop 970 via ports 1B and 2B, as indicated by direction arrows 683 and 684. The solvent may further carry the PSFs from port 2B via line 205 to the MWC 110. Meanwhile, further flow of PSFs from the aTREF column 25 is directed from line 204 into port 5B and on to port 6B as indicated by direction arrow 671. The flow from aTREF column 25 when SPIV 75 is in position IV sends the flow of PSFs to waste 58 from port 6B via line 220. In this way, flow of PSFs from an aTREF system 300 to a MWC 110 may be controlled by loading PSFs for the MWC 110 while the SPIV 75 is in position III, and injecting PSFs to the MWC 110 when the SPIV 75 is in position IV. Transitioning of the SPIV 75 between positions III and IV may be manually controlled or coupled to and controlled by the device controller 150 via connection 909.

In an embodiment, the MWC column 110 is less than about 20 cm in length and less than about 10 mm in diameter and allows samples to be fractionated in less than about 10 minutes thus the term rapid GPC. Examples of suitable columns include but are not limited to the PLgel 10 μM HTS-B column that is commercially available from Polymer Labs (Amherst, Mass.) and the HSPgel HT MB-H column that is commercially available from Waters (Milford, Mass.). Examples of suitable GPC devices that may be fitted to perform rapid GPC by one suitably skilled in the art include the Agilent 1100 Series SEC-GPC, commercially available from Agilent Inc., or the 150C SEC-GPC, commercially available from Waters and the PL220 GPC-SEC, commercially available from Polymer Labs.

In the embodiment of FIG. 2, PSFs eluting from the MWC column 110 are conveyed by line 213 into detection system 115. Detection system 115 may be manually controlled or coupled to and controlled by the device controller 150 as indicated by connection 910. The detection system may determine the molecular weight of the PSFs from the MWC column via an optical device. In an embodiment, such an optical device measures in the infrared range. In another embodiment, such an optical device measures differential refractive index. The PSFs from the MWC column may likewise be subjected to chemical composition analyses. Such chemical composition analyses may be carried out via FTIR, multiangle light scattering detector, a viscosity detector, or combinations thereof. PSFs eluting from detection system 115 are conveyed via line 207 to the waste collection vessel 58.

In one embodiment, the detection system 115 may comprise a differential refractometer (DRI), a Fourier transform infrared detector (FTIR), a multiangle light scattering detector (MALS), a viscometer (VISC), or any combination thereof. Suitable DRI, FTIR, VISC and MALS are those that would be used by one skilled in the art. These detectors may be in addition to or in lieu of detection system 55. For example, a detector array equivalent to detection system 55 could be placed in line 205 upstream of MWC 110 or in parallel with MWC 110 via a slip stream from line 205. Such an arrangement may greatly simplify synchronization of data for MPFs subject to rGPC analysis, as only the samples loaded and injected via SPIV 75 would be subject to analysis via detection system 115 and an equivalent detection system 55.

The aTREF-rGPC device of FIG. 2 employs a controller 150 in order to synchronize an aTREF system 300 and rGPC system 400 for characterization of a polymer sample. In an embodiment, the analysis of PSFs by detection systems 55 and 115 are synchronized, thereby providing compositional data and molecular weight distribution data for each given PSF. In an embodiment, the synchronization occurs in real time, and may be implemented via control system 150. For example, control system 150 may capture data from detection systems 55 and 115 at known intervals and match data for those intervals, for example by clock synchronization, a counter or other incrementing device, or other synchronization means.

In various embodiments, such synchronization may comprise: fractionating a polymer sample via temperature gradient; detecting the composition of sample fractions; separating polymers in the sample fractions based on differences in molecular weight; detecting the molecular weight and molecular weight distribution of polymers in the sample fractions; and characterizing the polymer sample based on concurrent determination of the composition, molecular weight and molecular weight distribution. Fractionating via temperature gradient may also be referred to as fractionating based on polymer crystallizability or fractionating via polymer dissolution temperature.

In embodiments, synchronization is achieved by employment of the controller 150 to coordinate a valve scheme comprising a SPIV 71 for injection of samples into the aTREF system 300, and another SPIV 75 for injection of samples into the rGPC system 400. The controller 150 may regulate the positions of valve 50 and SPIV 75 in order to concurrently receive molecular weight distribution and composition data for the same PSF from the detection systems 55 and 115. Meanwhile, the controller 150 may synchronize the determination of data via detection systems 55 and 115 with injections of new polymer samples into the aTREF system 300 via sample injection device 10 in order to achieve a fully integrated, on-line process. For example, a plurality of polymer samples may be made available via a corresponding plurality of polymer sample container 72 and means for automatically changing sample containers and for operating the syringe 74.

In an embodiment, the device controller 150 may send a programmed signal to the rGPC system 400 to begin internal countdown when a sample is introduced to the aTREF column 25, allowing for synchronization of the aTREF and rGPC fractionations. Alternatively, the aTREF system 300 and rGPC system 400 may be synchronized by the device controller 150, such that the device controller 150 signals the MWC column 110 to accept sample injections from the SPIV 75 at fixed time intervals typically corresponding to the cycle time of the MWC 110. Alternatively, the aTREF system 300 and rGPC system 400 may be synchronized by the device controller 150 signaling the MWC column 110 to accept sample injections from the SPIV 75 at user defined intervals or profile, for example at predefined aTREF elution temperatures.

In an embodiment, the device controller 150 may be a computer running software capable of synchronizing the data acquired from both the rGPC and aTREF fractionations. In an embodiment, a suitable computer is a digital computer, such as an IBM Intel Pentium-based personal computer, capable of receiving input from multiple detectors through serial interfaces. The computer may also be capable of receiving user input through a standard keyboard or another computer. In an embodiment depicted in FIG. 6, the user interface of the systems controller device 150 may display the results of the rGPC and aTREF analysis as individual plots along with a contour plot of the synchronized analysis providing for example at any given elution temperature a corresponding molecular weight distribution profile and, at any given molecular weight a corresponding aTREF profile. The resultant analytical data may be displayed in a plurality of windows which may be sized and arranged in a variety of configurations on the user interface (e.g., display screen).

Figure 6:
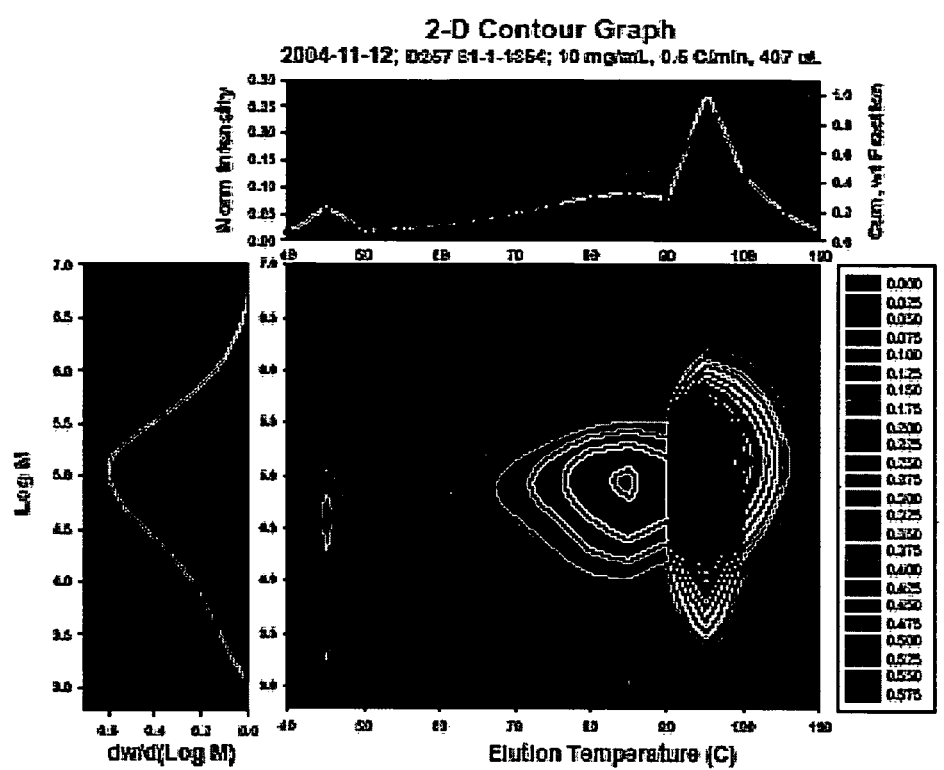
FIG. 6 is a color graphical representation of data obtained from an aTREF-rGPC device.

Referring to FIG. 6, displayed in the upper window is an overall aTREF profile for the entire polymer sample. In an alternative embodiment, the upper window may depict the aTREF profile for a portion of the polymer sample, for example a portion having a particular molecular weight. Referring again to FIG. 6, displayed in the lower left window is the overall molecular weight distribution profile for the full polymer sample. In an alternative embodiment, the lower left window may depict the molecular weight distribution profile for an aTREF slice at a given elution temperature. The contour level in the lower right window of FIG. 6 depicts the product of the normalized weight fraction of an aTREF slice times the differential intensity (i.e $dw/d(Log\ M)$) in a molecular weight distribution profile at a given molecular weight.

In an embodiment, the aTREF-rGPC device synchronization of the results of the aTREF fractionation and rGPC separation provides an online continuous two dimensional process where each rGPC slice represents the composition of the aTREF eluent for a temperature range of less than about 0.05° C. In some embodiments, a complete two-dimensional analysis of a polymeric sample by the disclosed aTREF-rGPC device can be carried out in less than about 24 hours, alternatively, less than about 20 hours, alternatively less than about 16 hours, alternatively less than about 12 hours, or alternatively less than about 8 hours.

EXAMPLES

The invention having been generally described, the following examples are given as particular embodiments of the invention and to demonstrate the practice and advantages thereof. It is understood that the examples are given by way of illustration and are not intended to limit the specification of the claims to follow in any manner.

Example 1

A computerized simulation of aTREF-rGPC apparatus and method described above was prepared and used to simulate fractionation of a polymer sample containing a short-chain branched polyethylene resin such as the traditional low density polyethylene (LDPE) resin or the Chevron Phillips Chemical Company LP, linear low density polyethylene (LLDPE)-type resins. rGPC data acquisition and data processing software were PE Nelson (Model 2600 Multiple Instrument Chromatography Software 1988-1992, Perkin Elmer Corp.) and the Chevron Phillips Chemical in-house DRPolymer Software. However, commercially available software may be used. An example of suitable software for data processing and acquisition is the Cirrus Multidetector Software commercially available from Polymer Laboratories. Graphical Software used for the 3D plot was SigmaPlot for Windows Version 4.0 from SPSS Inc.

The LLPDE samples are composed of branched molecules with various levels of single chain branching. During the simulation LLPDE resin is dissolved in 1,2,4-trichlorobenzene. As illustrated by FIG. 2, solubilized LLPDE was injected at sample injection device 10 at a solvent flow rate of 0.5 ml/min. The LLPDE sample was loaded onto an aTREF column that was 6 inches (152 mm) in length with an internal diameter of 0.5 inches (12 mm), and packed with #30 SS Shot obtained from Vulcan Blast Technology. The computer was programmed to ramp the temperature at a rate of 0.5-1.5°

C./min with a temperature ramping range of 35° C. to 125° C. and a total ramping time of between 60 to 180 minutes.

LLPDE fractions eluting from the aTREF column were injected onto the rGPC column via the SPIV 75 at temperatures of 35, 40, 45, 50, 55, 65, 75, 85, 95, 105 and 110° C. The rGPC column was a PL Rapide column commercially available from Polymer Labs that was 10 cm in length and 10 mm in diameter. The SPIV 75 had an injector loop 970 size in the range of 100 μl to 500 μl. LLPDE samples loaded onto the rGPC column were run at a flow rate of 0.5-1.0 ml/min at a temperature of 140° C. rGPC data acquisition software recorded polymer concentration as a function of elution time. aTREF data acquisition software recorded chemical composition data as a function of elution temperature.

Since the flow rate of the rGPC system is a constant, a raw chromatogram is a plot of concentration c as a function of elution volume $V_e$. In order to convert the raw chromatogram into the MWD profile, a calibration is performed using a set of narrow MWD polymers whose MW are already known under the same run conditions used to fractionated the LLPDE sample. A calibration curve, Log M vs. elution volume $V_e$ for the standard can then be established. Coupling the raw chromatogram ($c$–$V_e$) with the calibration curve, Log M–$V_e$, elution volumes in the raw chromatogram can be converted into Log M. Using the following equation, the number average MW ($M_n$), weight average and polydispersity index ($M_w/M_n$) can be calculated.

$$M_n = \Sigma(c_i)/\Sigma(c_i/M_i)$$

$$M_w = \Sigma(c_i/M_i)/\Sigma(c_i)$$

Figure 7:
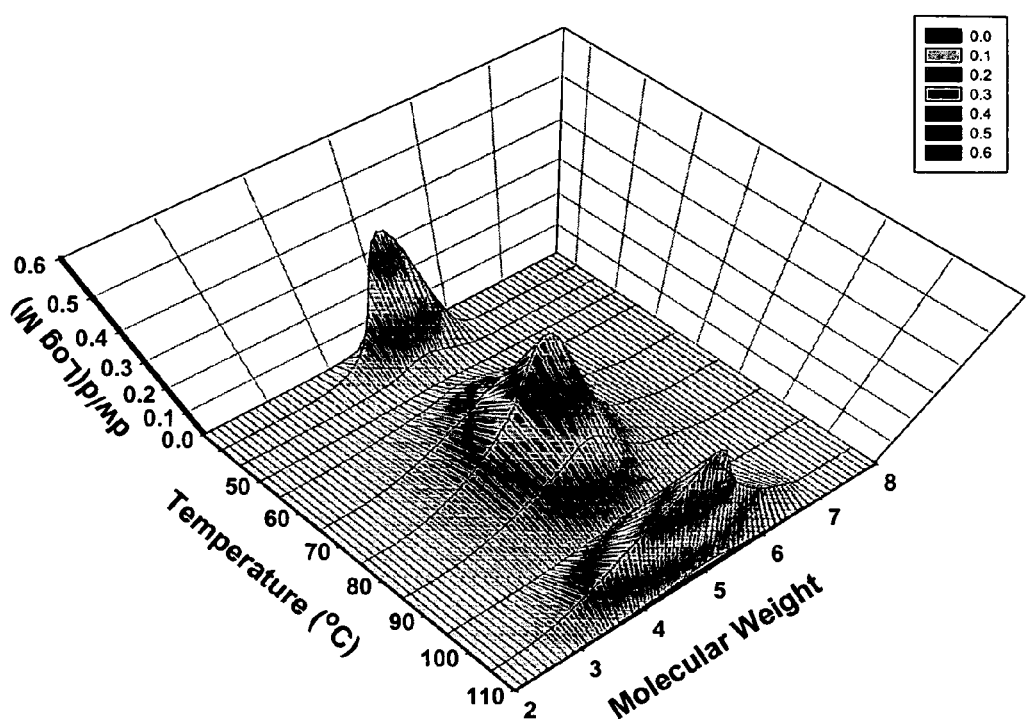
FIG. 7 is a two dimensional color graphical representation of a polymer sample characterized by the aTREF-rGPC device.
Figure 8:
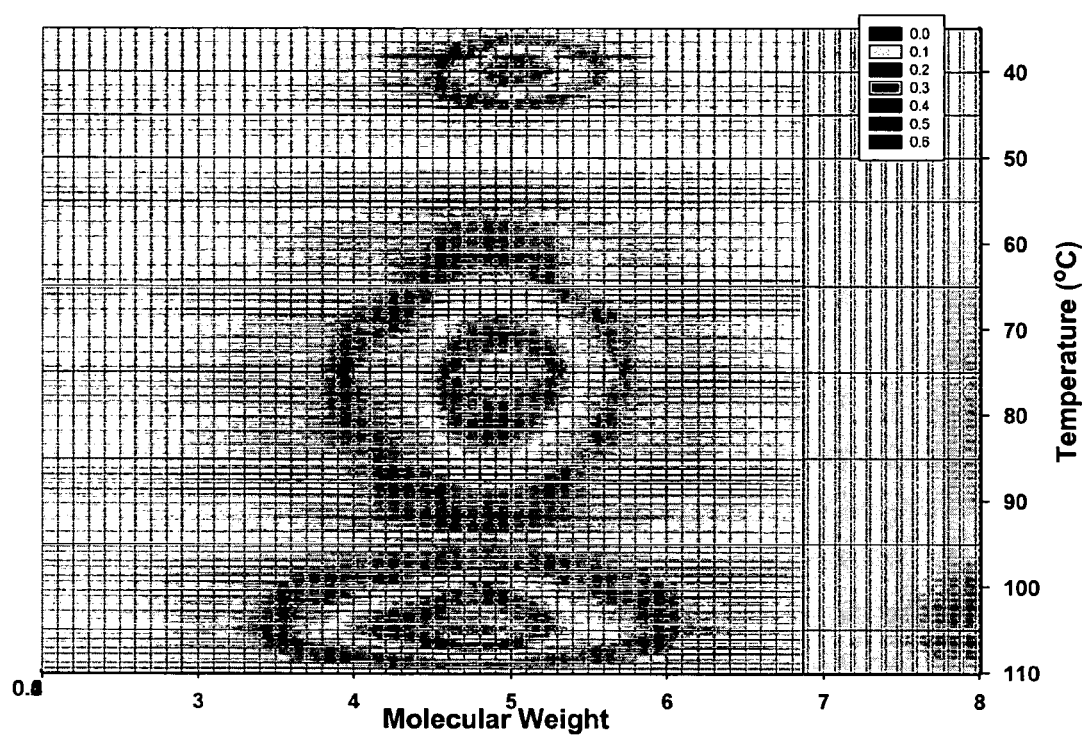
FIG. 8 represents a color graphical contour profile of data obtained from characterization of a polymer sample by an aTREF-rGPC.
Figure 9:
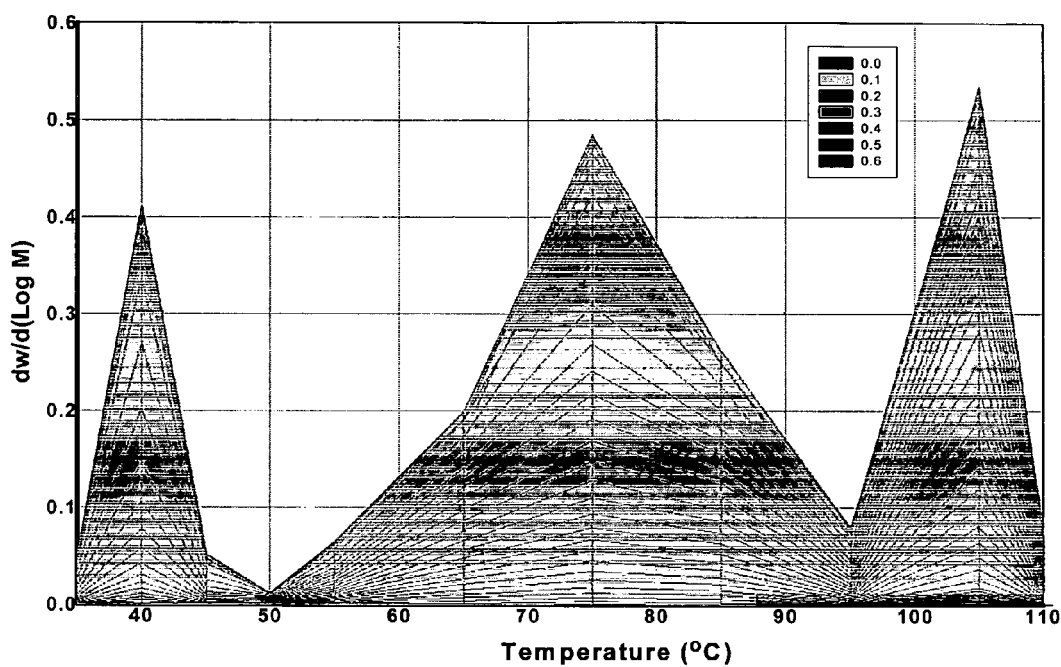
FIG. 9 is a two dimensional color graphical representation of data obtained from characterization of a polymer sample by an aTREF-rGPC.

The digitized rGPC data were saved as the concentration-elution time (volume) data pairs on computer storage devices with various data structures FIG. 7 is a two dimensional plot of fractionation of the LLDPE resin using the simulation of aTREF-rGPC apparatus diagrammed in FIG. 2. The two dimensional data set shown in FIG. 7 was constructed by plotting elution temperature (temperature) v. molecular weight v. weighted weight fraction (dw/d(log M)). The simulated aTREF-rGPC apparatus fractionated the LLPDE sample into three peaks. Peak 1 is the narrow peak at approximately 40° C. in FIG. 7 and corresponds to the room temperature soluble fraction of the LLPDE sample. The room temperature soluble fraction of the LLPDE sample contains highly branched polymers that do not crystallize even at room temperature. Peak 2 is the broad peak in the middle temperature range occurring at approx. 75° C. and corresponds to a fraction of the LLPDE sample that consists of branched molecules with various single-chain branching content. Peak 3 is a sharp peak observed at approximately 105° C. and corresponds to a fraction of the LLPDE sample that consists of high-density polyethylene and polyethylene homopolymers. Projecting the 3D data to the x-y plane resulted in the temperature-molecular weight contour plot, FIG. 8. Similarly projecting the 3D data to the x-z or y-z planes resulted in the normal MWD and concentration-elution temperature profiles, FIG. 9.

Examples 2-6

Polymer samples were separated and analyzed using an aTREF-rGPC device of the type disclosed herein. Basic polymer properties and run conditions for the polymer samples separated and analyzed are presented in Table 1.

TABLE 1

Table I: Basic Resin Properties and Major Run Conditions

| | | | | | Major Run Conditions | |
|---|---|---|---|---|---|---|
| | | | | | TREF Conditions | |
| Sample ID | Resin Type | MI g/10 min | Density g/c.c. | Polymer Concentration mg/mL | Temp. Cooling Rate Range ° C./min ° C. | Duration of Heating Elution Holding at RT min ° C./min ° C. mL/min | Temp. Rate Range Rate | GPC Conditions Pump Injection Rate Volume Temp. mL/min mL ° C. |
| A | Ziegler-Natta Polyethylene (Z-N PE) | na | 0.921 | 5 | 1.0<br>125-40 | ≥60<br>0.2<br>40-120<br>0.981 | 0.6<br>0.1<br>145 |
| B | Chrome Polyethylene (Cr-PE) | 0.2 | 0.923 | 10 | 0.5<br>145-40 | ≥60<br>0.5<br>40-145<br>0.975 | 0.6<br>0.4<br>145 |
| C | Metallocene Polyethylene (mPE) | 1.0 | 0.918 | 5 | 1.0<br>125-40 | ≥60<br>0.2<br>40-130<br>0.970 | 0.6<br>0.1<br>145 |
| D | mPE/mPE Blend | (0.8) | (0.931) | 5 | 1.0<br>125-40 | ≥60<br>0.2<br>40-130<br>0.970 | 0.6<br>0.1<br>145 |
| E | Z-N PE/Z-N PE Blend | 0.1 | 0.961 | 5 | 1.0<br>125-40 | ≥60<br>0.2<br>40-130<br>0.975 | 0.6<br>0.1<br>145 |

Example 2

Figure 10:
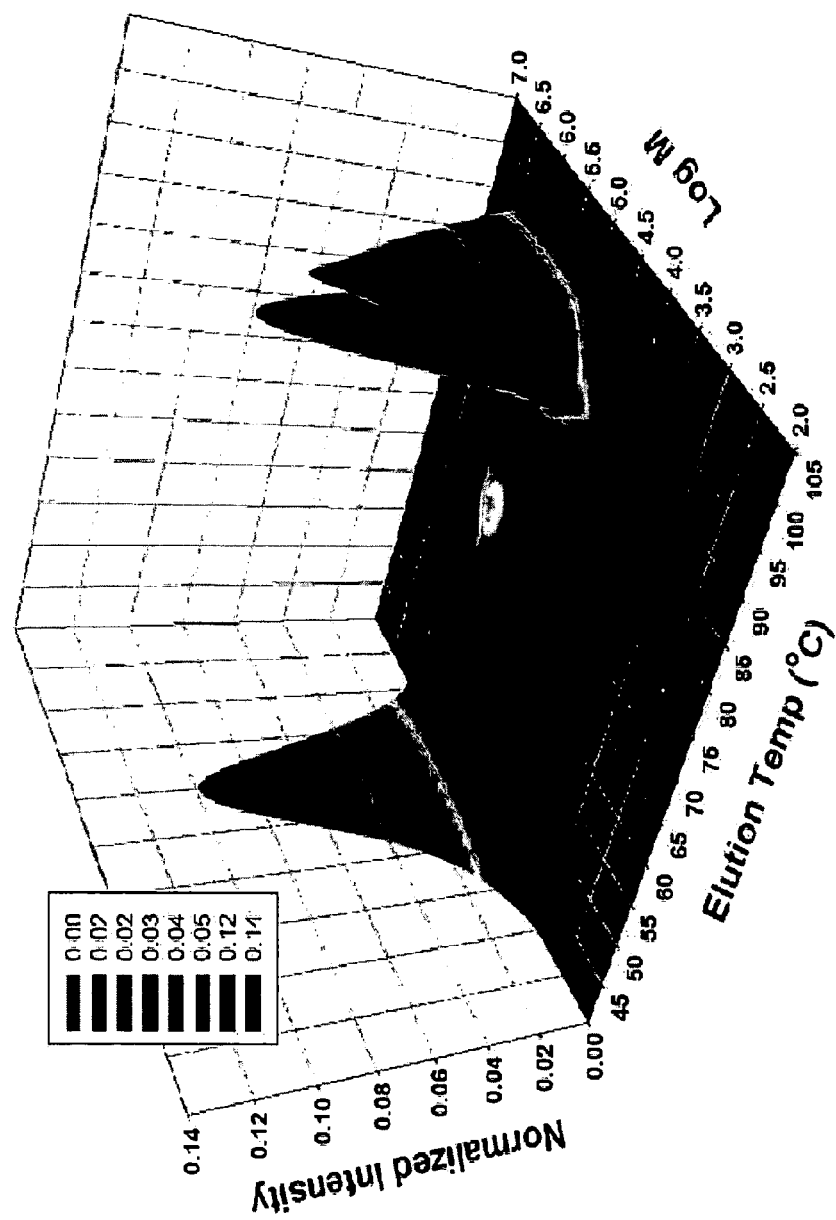
FIG. 10 is a three dimensional presentation of the aTREF-rGPC data for sample A in Example 2.

Sample A was separated and analyzed using an aTREF-rGPC apparatus of the type disclosed herein. Sample A was a conventional linear low-density polyethylene (LLDPE) resin with a density of 0.921 g/cc and was produced using a Ziegler-Natta catalyst. Plotted in FIG. 10 is a three-dimensional presentation of the 2-D aTREF-rGPC dataset for Sample A under the run conditions listed in Table I. Note that in FIG. 10 the x-axis is the elution temperature, the y-axis is the molecular weight in logarithmic scale, and z-axis is the normalized intensity that is a product of the weight fraction of an aTREF slice and the differential intensity of a MWD slice (i.e. dw/d (Log M)) at a given molecular weight. FIG. 10 is a "snapshot" of the 3-D plot at a rotating angle. The results demonstrate there are three regions (or zones) in FIG. 10: a low temperature peak that corresponds to the room-temperature (RT) soluble fraction; a broad peak at the mid temperature region peaked at about 75° C. that is believed to be originated from the linear low-density (LLD) component; and a double peak in the high temperature region ranging from about 85° C. to 105° C. This third peak corresponds to high-density polyethylene and homopolymer-like components, respectively, for peaks at about 92° C. and at about 96° C.

Figure 11:
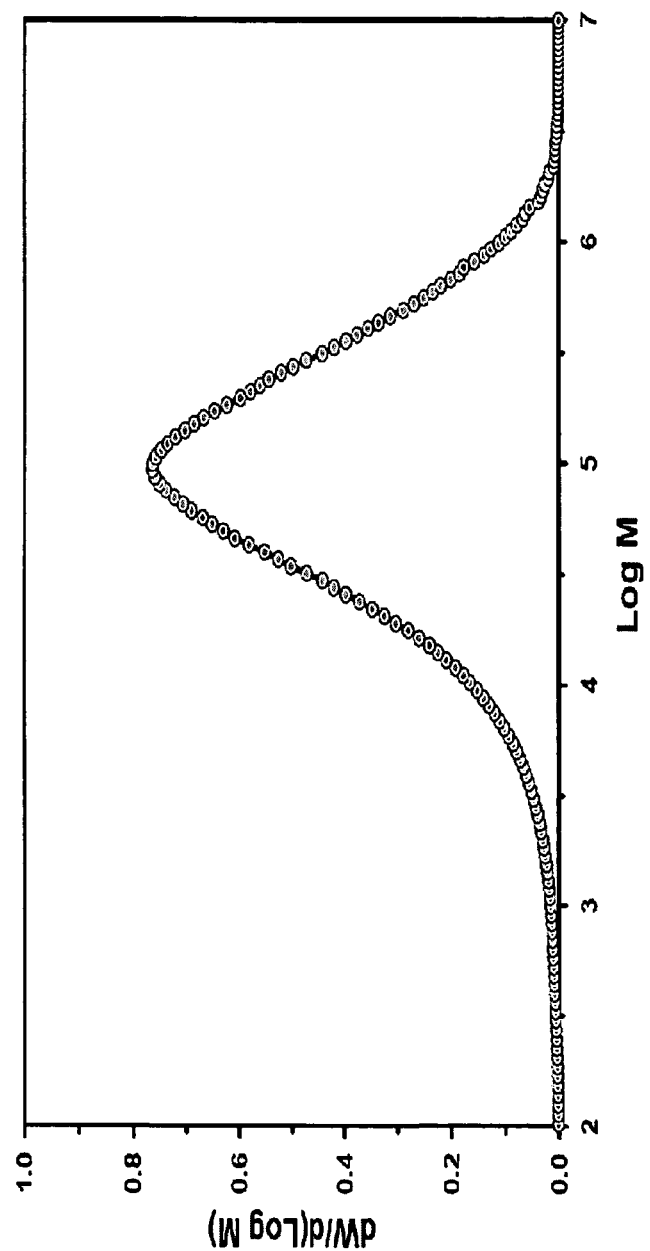
FIG. 11 is a plot of the overall molecular weight distribution profile for Sample A in Example 2.

In FIG. 11 is plotted the overall molecular weight distribution (MWD) profile of the full polymer of Sample A. This overall MWD profile is a projection of the 3-D plot in FIG. 10 to its y-z plane and it is the sum of the MWD profiles of all aTREF slices presented in FIG. 10. The overall aTREF profile of Sample A is plotted in FIG. 12; it is a projection of all the aTREF profiles in the 3-D plot in FIG. 10 to its x-z plane. This overall aTREF profile is a sum of aTREF profiles of all MWD slices. Note that this overall aTREF slice can also be obtained independently via the detection unit 55 (see FIG. 4) in a continuous manner.

Figure 12:
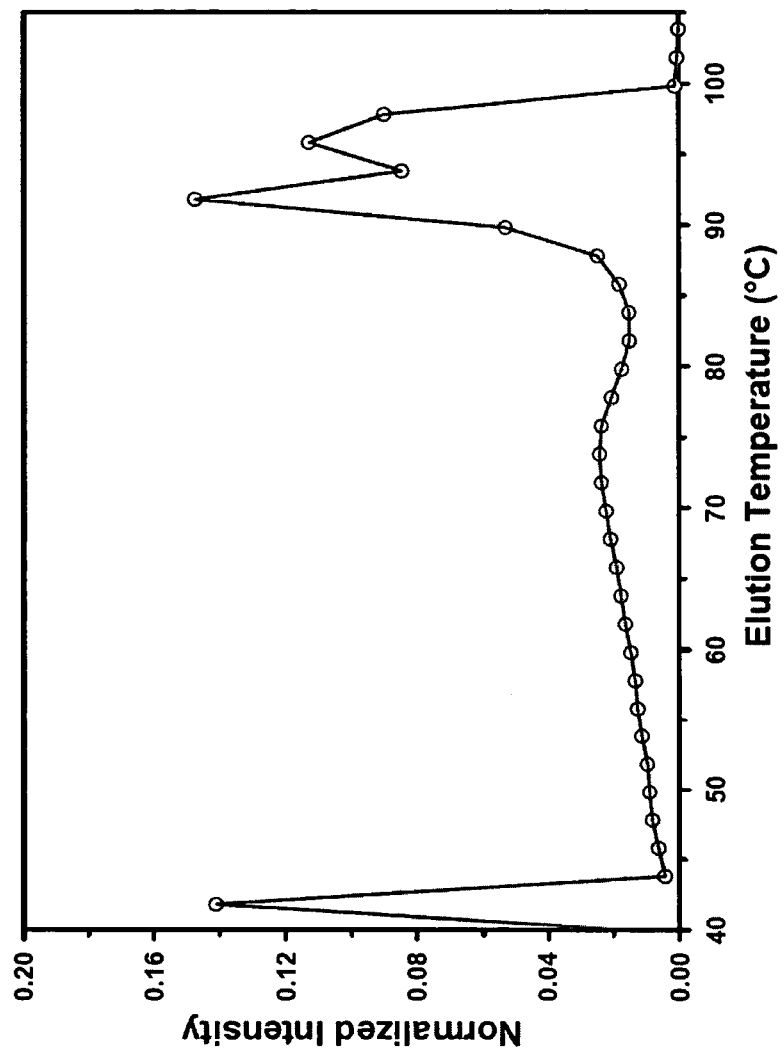
FIG. 12 is a plot of the overall aTREF profile for Sample A in Example 2.
Figure 13:
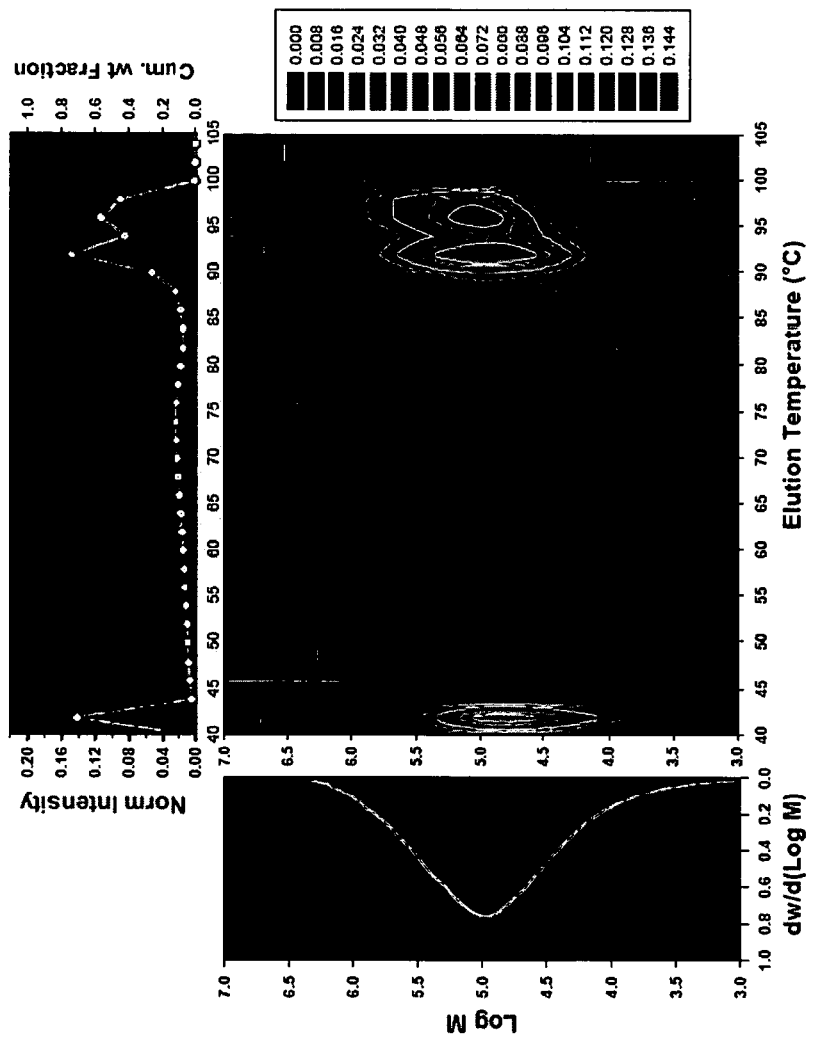
FIG. 13 is a two dimensional contour plot for Sample A in Example 2.

The lower right window in FIG. 13 is a 2-D contour plot for Sample A. This 2-D contour plot is a projection of the 3-D plot in FIG. 10 to its x-y plane, in which the color-coded contour level represents the normalized intensity as shown in the z-axis in FIG. 10. The upper window and the left window in FIG. 13 are the aTREF window and MWD window, respectively. The left y-axis of the aTREF window plots the normalized intensity as a function of elution temperature while the right y-axis plots the cumulative weight fraction as a function of elution temperature. The aTREF window can plot the overall aTREF profile of the full polymer as shown in FIG. 12 or an aTREF profile for polymer with a same given molecular weight. Similarly, the MWD window can plot the overall MWD profile of the full polymer as shown in FIG. 11 or the MWD profile of an aTREF slice at a given elution temperature.

The three zones (regions) shown in FIG. 10, i.e. the low temperature RT soluble zone, the mid-temperature LLD zone, and the double-peaked high temperature HDPE/homopolymer-like zone, can also be seen in FIG. 13.

Figure 14:
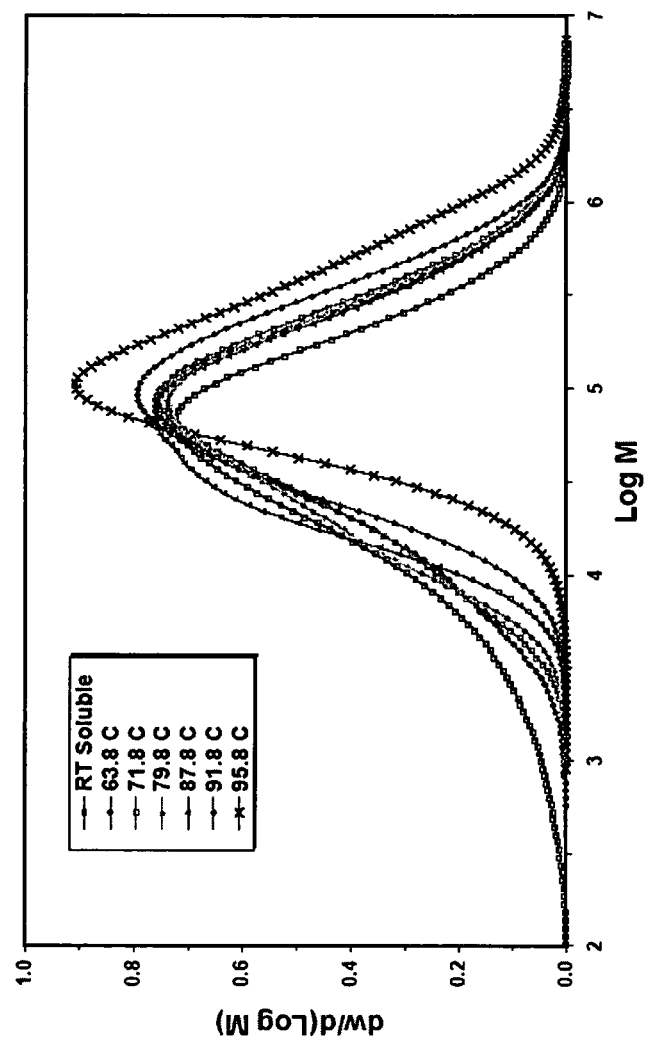
FIG. 14 is a plot of the molecular weight distribution profiles of aTREF slices of Sample A in Example 2.
Figure 15:
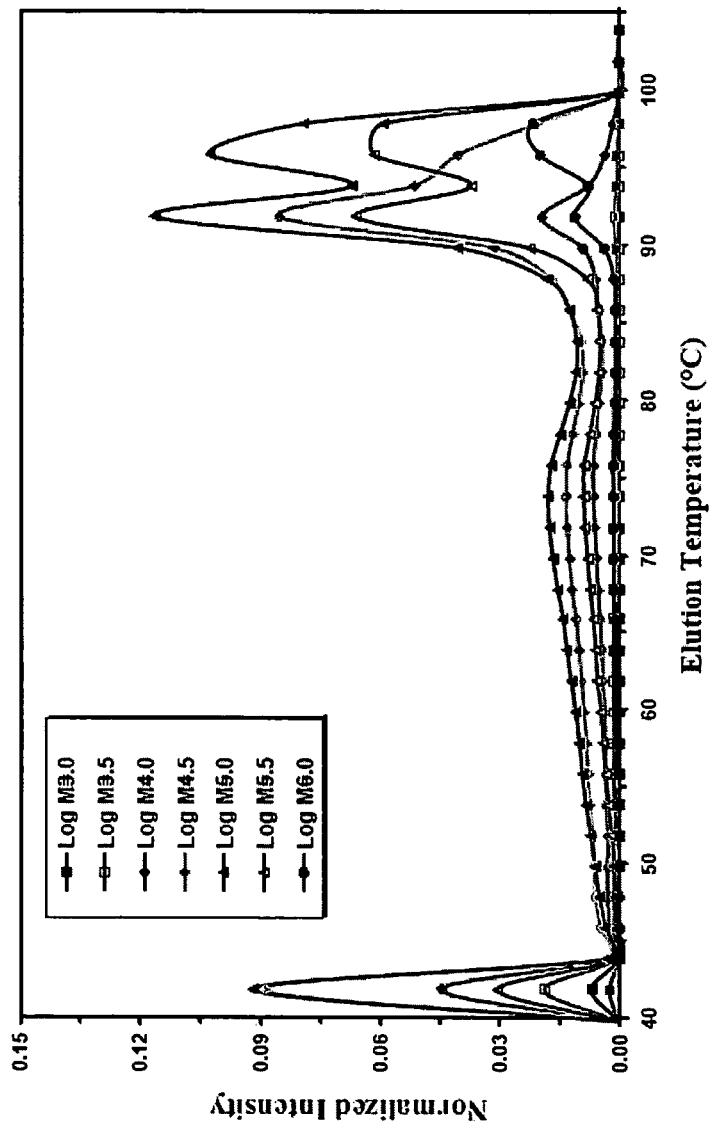
FIG. 15 is a plot of aTREF slices at a given molecular weight for Sample A in Example 2.

In FIG. 14 are plotted the MWD profiles of aTREF slices of Sample A at the given elution temperatures. FIG. 14 shows that the RT soluble fraction contains large amount of high molecular weight components, not simply low MW component. In general, all the MWD slices are broad regardless of elution temperature. At higher elution temperatures, such as the slice at 95.8° C., it contains more high-molecular weight components but their MW distribution is narrower, i.e. with smaller polydispersity index, Mw/Mn.

aTREF slices of Sample A at given molecular weights are plotted in FIG. 15, in which the x-axis is the elution temperature and the y-axis is the normalized intensity at the given temperature. Data plotted in FIG. 15 were extracted from the same data matrix used for FIG. 10. FIG. 15 shows that a large sample heterogeneity was observed at various MW. For example, at a given molecular weight of 100,000 g/mol (i.e. Log M=5.0), there is a broad chemical composition distribution (CCD) present for the macromolecules of the same MW, due largely to the heterogeneity of short-chain branching distribution in the polymer. At this MW, about 13 wt % of the polymer is in the soluble fraction, about 30 wt % of the polymer in the liner low-density (LLD) region, about 33 wt % of the polymer in the HDPE region, and about 24 wt % of the polymer in the homopolymer-like region. For different molecular weights, their aTREF profiles vary significantly. For example, comparing the aTREF slices at Log M=4.5 and Log M=6.0, the former has much higher soluble and LLD components while the latter has much higher homopolymer-like component.

The results demonstrate the aTREF-rGPC apparatus is a powerful tool for the characterization of a polymer sample. The type of information plotted in FIG. 15 cannot be readily obtained by other means unless a cross-fractionation is performed. Cross-fractionation refers subjecting the polymer to solvent-gradient fractionation (SGF) to separate the polymer according to its molecular weight before an aTREF fractionation is carried out on each and every one of the SGF fractions that have been characterized off-line, which is a very tedious process.

Example 3

Sample B was separated and analyzed using an aTREF-rGPC apparatus of the type disclosed herein. Sample B is a chromium catalyst-based low-density linear polyethylene (LDLPE) resin with a density of 0.923 g/cc.

Figure 16:
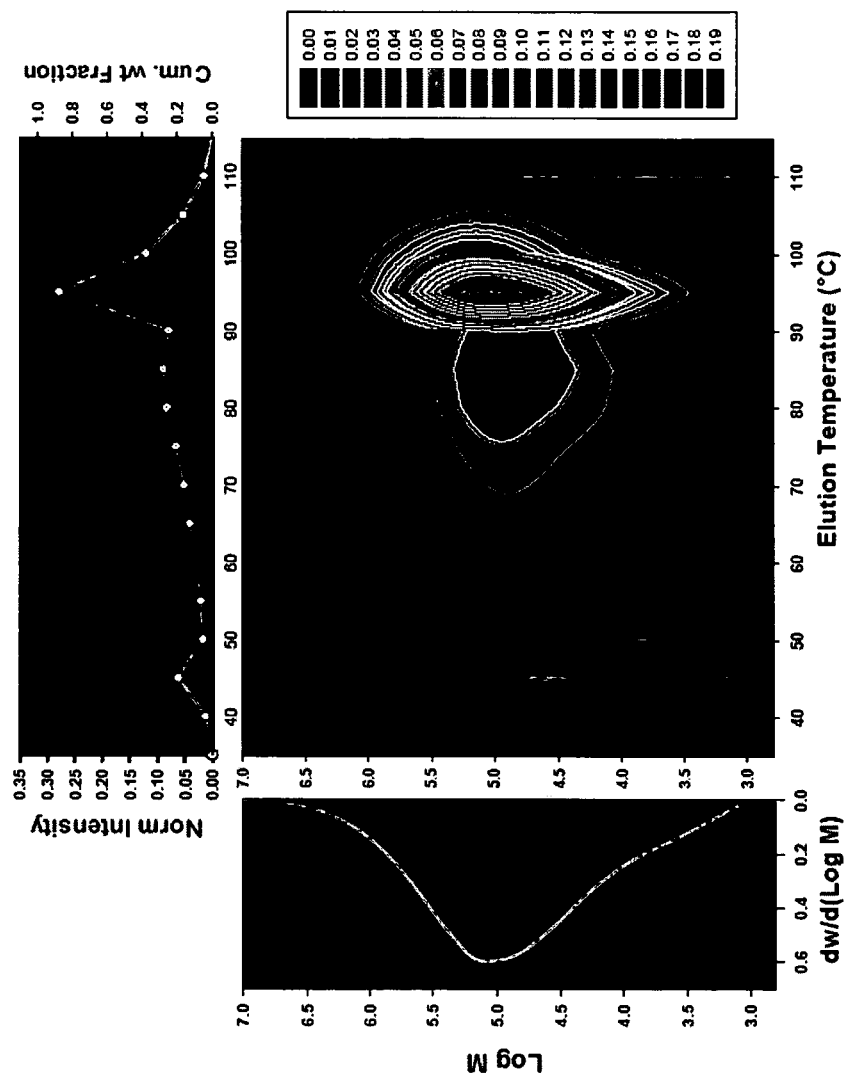
FIG. 16 is a two-dimensional contour graph for Sample B in Example 3.

Plotted in FIG. 16 is a 2-D contour graph for Sample B run under the conditions listed in Table I. There are three regions shown in FIG. 16, i.e. the soluble fraction peak, the broad linear low-density (LLD) peak, and the high-density/homopolymer-like region; However in comparison to Sample A, Sample B contains less room temperature (RT) soluble fraction and the soluble fraction has smaller molecular weight. Furthermore, Sample B contains a higher amount of LLD fraction. Due to differences in run conditions, the dataset used to produce FIG. 16 has less resolution when compared to a similar dataset generated for Sample A, see FIG. 13. Referring to FIG. 13, the aTREF profile in the upper window, in which broader aTREF peaks are observed and the double in FIG. 13 has degenerated into one single much broader peak. Note that Sample B is run under higher polymer concentration, larger rGPC injection volume and, a slower cooling rate but higher heating rate during aTREF elution as compared to Sample A Example 4

Figure 17:
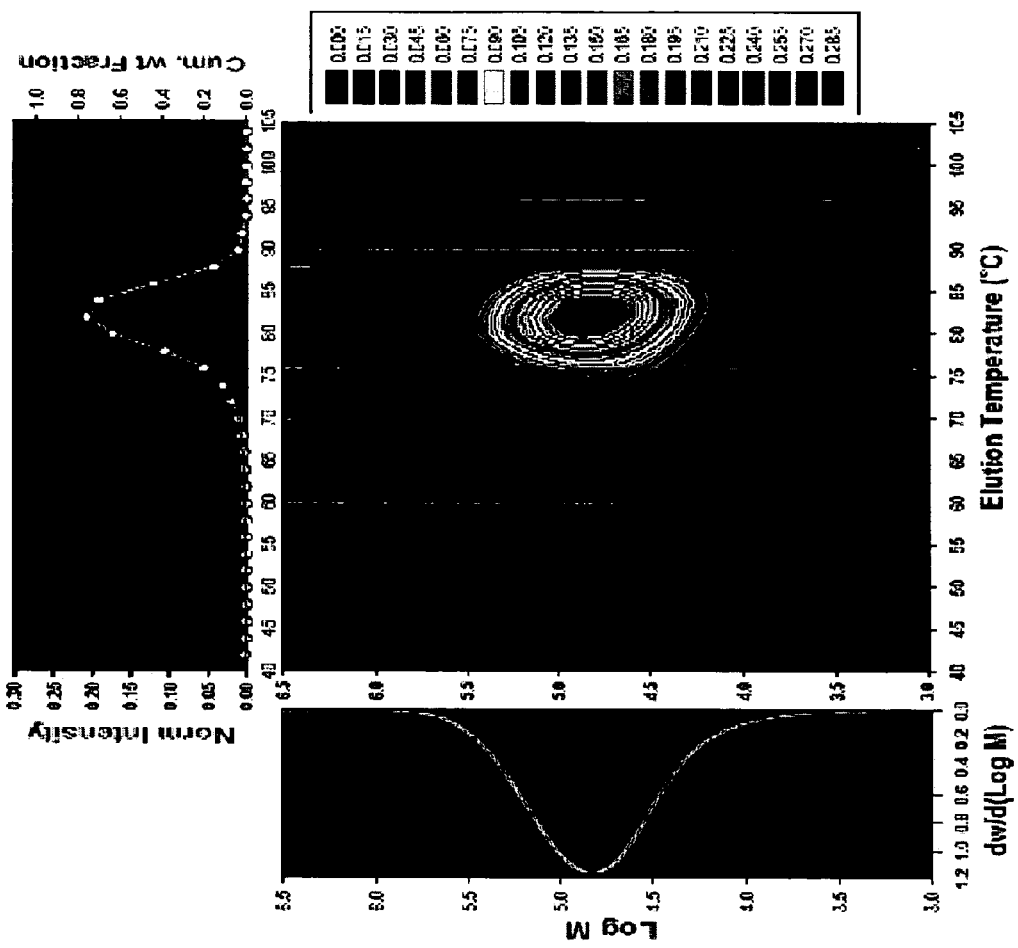
FIG. 17 is a two-dimensional contour graph for Sample C in Example 4.

Sample C was separated and analyzed using an aTREF-rGPC apparatus of the type disclosed herein. Sample C is a metallocene-catalyzed linear low-density polyethylene (mLLDPE) resin made with proprietary technology from Chevron Phillips Chemical Company and having a density of 0.918 g/cc. Plotted in FIG. 17 is a 2-D contour graph for Sample C run under the conditions listed in Table 1. The graph shows an extremely low soluble fraction having a very low molecular weight and very narrow molecular weight distribution.

The results in FIG. 17 when compared to conventional LLDPE (Sample A) and Cr-LDLPE (Sample B) shows a very homogeneous chemical composition regardless of the component molecular weight. However, Sample C contains small amounts of a low molecular weight component which likely has the same chemical composition as the high molecular component, although the low MW component eluted at lower temperatures due to the chain-end effect. FIG. 17 also clearly shows there is no HDPE or homopolymer-like components which is a result that is in agreement with the literature suggesting the homogeneous nature of metallocene resins.

Example 5

Figure 18:
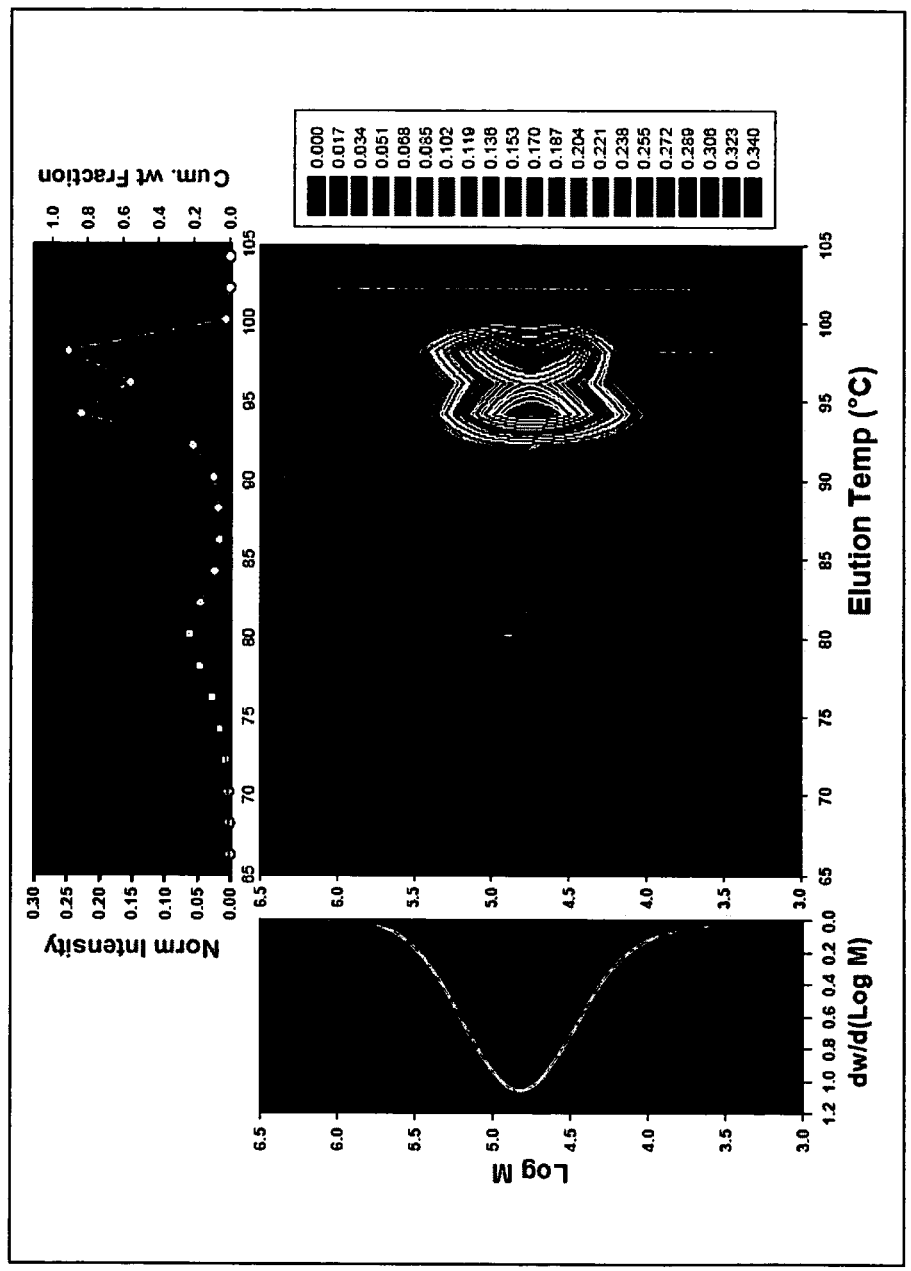
FIG. 18 is a two-dimensional contour graph for Sample D in Example 5.

Sample D was separated and analyzed using an aTREF-rGPC apparatus of the type disclosed herein. Sample D is a 50:50 blend of two metallocene resins having very similar molecular weight and molecular weight distribution but with different densities. FIG. 18 is a 2-D contour graph for Sample D run under the conditions listed in Table I. The results show that one of the components in Sample D is Sample C, an mLLDPE, and the other is also a metallocene resin but essentially is a homopolymer. Furthermore, although the molecular weight distribution of the polymer blend looks like a normal metallocene resin with narrow MWD, it has considerable chemical composition heterogeneity. Also Sample D contains low soluble fraction as in Sample C and the soluble fraction also has very low MW and narrow MWD (data not shown). FIG. 18, the 2-D profile shows three peaks: one peak at about 80° C. in the LLD region, and another peaked at about 94° C. in the high-density polyethylene (HDPE) region, and yet another peaked at 98° C. in the homopolymer-like region. In Sample D, the LLD peak is shifted to lower temperature as compared to FIG. 17. This peak also has reduced total intensity (about 30%) as compared to the initial content (50%). Clearly, some of the component of Sample C in this blend elutes at higher temperatures. This result suggests some interaction, likely co-crystallization, may have occurred between these two components in Sample D. The results demonstrate that the inventive method and device disclosed herein can be used for the study of polymer blends.

Example 6

Figure 19:
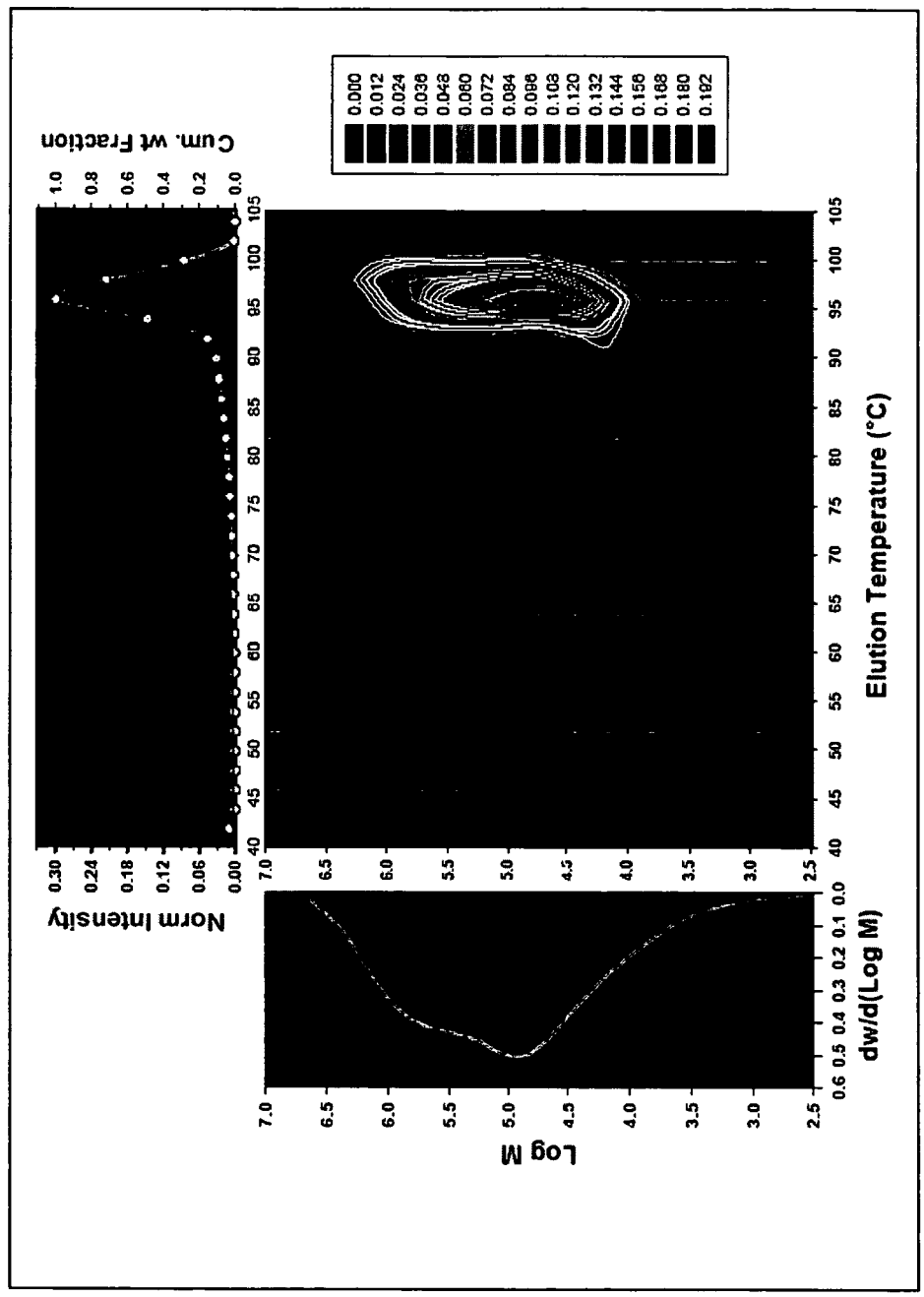
FIG. 19 is a two-dimensional contour graph for Sample E in Example 6.

Sample E was separated and analyzed using an aTREF-rGPC apparatus of the type disclosed herein. Sample E is a bimodal HDPE with a density of 0.961 g/cc consisting of two components: one is a high-MW copolymer and the other is a low-MW homopolymer, both of which are made with a conventional Ziegler-Natta catalyst. Plotted in FIG. 19 is a 2-D contour graph for Sample E run under conditions listed in Table I. FIG. 19 demonstrates that as expected for HDPE, Sample E contains low amount of RT-soluble fraction that has both a low MW and narrow MWD. The majority of components (about 80%) in Sample E are eluted out at the HDPE and homopolymer-like region (90° C.-105° C.). In this region, as the elution temperature increases, the dominating low-MW narrow peak is replaced by high-MW component. The high-MW component from the copolymer component co-elute with the high-MW component from the low-MW homopolymer. Furthermore, for Sample E there is about 20% of polymer eluting at temperatures below 90° C., as can be realized from the TREF profile in the upper window. These low temperature fractions spread across a large temperature range, resulting in low concentration for each fraction. As a result, their polymer compositions are not clearly shown at the given contour level in FIG. 19. Therefore, in order to see the chemical composition of low concentration components, lowering the contour level is necessary.

Figure 20:
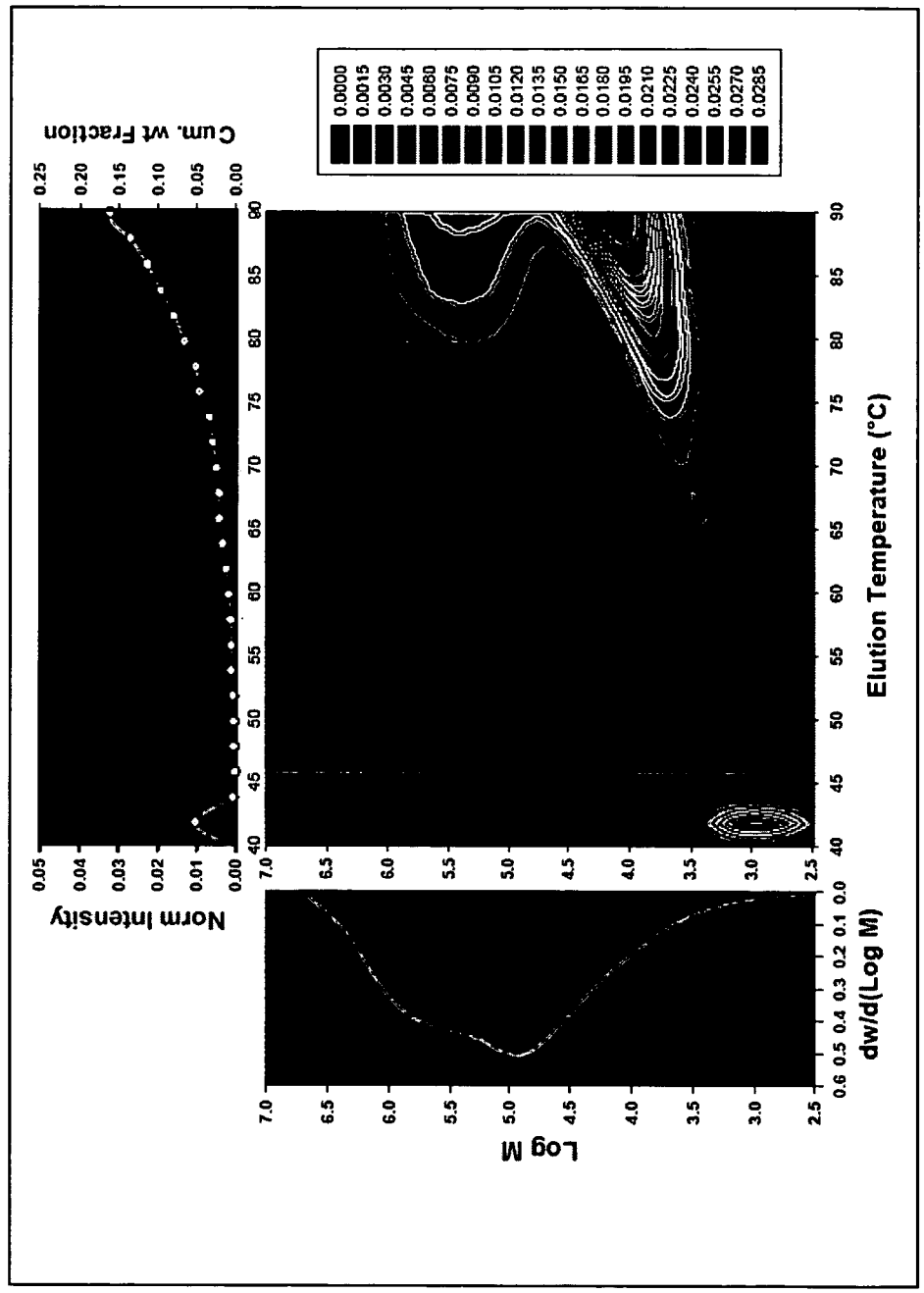
FIG. 20 is a two-dimensional contour graph in a limited temperature range for Sample E in Example 6.

Plotted in FIG. 20 is a part of FIG. 19 but with lowered contour level and limited temperature range (40° C.-90° C.). At the lowered contour level, it is clear that the components eluting at low temperatures are bimodals. The high molecular weight species in these bimodals, presumably from the high-MW copolymer component, co-elute at the given temperatures with species in the low-MW homopolymer component. This result and that in FIG. 19 strongly suggests that there is a high compositional heterogeneity present in the high-MW copolymer component in Sample E. Polymers with significantly different composition can co-elute together as long as they have the same crystallizability. The results demonstrate that the inventive methods and devices disclosed herein can also be used for the study of high performance resin with tailored chemical composition.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent that they provide exemplary, procedural or other details supplementary to those set forth herein.

What is claimed is:

1. An analytical method comprising:
   (a) performing, in a first device, a first fractionation of a polymer sample based on differences in crystallizability to provide a first sample fraction wherein the first fractionation is temperature rising elution fractionation;
   (b) splitting the first sample fraction into a first portion and a second portion;
   (c) performing a first analysis on the first portion of the first sample fraction;
   (d) conveying the second portion of the first sample fraction from the first device to a second device;
   (e) performing, in the second device, a second fractionation of the second portion of the first sample fraction to produce a second sample fraction wherein the second fractionation is rapid gel permeation chromatography; and
   (f) performing a second analysis on the second sample fraction.

2. The method of claim 1 wherein the polymer sample comprises a semicrystalline polymer, a polymer blend, a polymer whose solubility changes as a function of solvent temperature or combinations thereof.

3. The method of claim 1 wherein the first analysis comprises determining chemical composition.

4. The method of claim 1 wherein the second fractionation is based on hydrodynamic volume.

5. The method of claim 1 further comprising heating the first sample fraction, the second portion of the first sample fraction, or a combination thereof prior to the rapid gel permeation chromatography.

6. The method of claim 1 wherein the second analysis comprises determining molecular weight, molecular weight average, molecular weight distribution or combinations thereof.

7. The method of claim 1 implemented via a computer controlled device.

8. The method of claim 1 further comprising graphically representing the polymer composition, molecular weight, and molecular weight distribution of the polymer sample.

9. The method of claim 1 wherein the second fractionation is performed in less than about 10 minutes.

10. A device for characterizing a polymer sample comprising:
a first column for fractionating the polymer sample based on differences in crystallizability to obtain a first sample fraction;
a first detection device in fluid communication with the first column and receiving a first portion of the first sample fraction;
a second column in fluid communication with the first column and receiving a second portion of the first sample fraction from the first column, wherein the second portion of the first sample fraction is fractionated to produce a second sample fraction, wherein the second column comprises a rapid gel permeation chromatography column; and
a second detection device in fluid communication with the second column and receiving at least a portion of the second sample fraction.

11. The device of claim 10 wherein the first column is an analytical temperature rising elution fractionation column.

12. The device of claim 10 wherein the first detection device comprises a spectrometer, a photometer, a viscometer, or combinations thereof, which measures a composition of the first portion of the first sample fraction.

13. The device of claim 10 wherein the second detection device is an optical device which measures a molecular weight of the portion of the second sample fraction.

14. The device of claim 10 wherein the first detection device comprises a Fourier transform infrared detector, a multiangle light scattering detector, a viscometer, or combinations thereof and the second detection device comprises an infrared measuring device, a differential refractometer, or combinations thereof.

15. The device of claim 10 further comprising a computer coupled to the first and second columns and the first and second detection devices.

16. The device of claim 10 further comprising a hydrophobic interaction column, an ion exchange column, a high performance liquid chromatography column or combinations thereof in fluid communication with the first detection device, the first column or both.

17. The device of claim 10 wherein the rapid gel permeation chromatography column produces the second sample fraction in less than about 10 minutes.

18. The device of claim 10 wherein the first column is coupled to a first pump for conveyance of fluid thereto, the second column is coupled to a second pump for conveyance of fluid thereto, and the second column is in fluid communication with the first column via a hot transfer line.

19. The device of claim 18 wherein the first pump and the second pump are coupled to a reservoir.

20. The device of claim 18 wherein the first pump and the second pump are positioned within a housing or an assembly.

21. The device of claim 18 wherein the first pump is controlled by a controller independent of the second pump.

22. The device of claim 10 further comprising at least one multi-port valve conveying samples from a sample reservoir to the first column, conveying the second portion of the first sample fraction to the second column, or combinations thereof.

23. The device of claim 22 wherein the multi-port valve comprises at least six ports.

24. An analytical method comprising:
introducing a sample to an analytical device having an analytical temperature rising elution fractionation element and a rapid gel permeation chromatography element;
eluting a sample fraction with the analytical temperature rising elution fractionation element;
conveying a first portion of the sample fraction from the analytical temperature rising elution fractionation element to a detector;
conveying a second portion of the sample fraction from the analytical temperature rising elution fractionation element to the rapid gel permeation chromatography element;
determining the composition of the first portion in the detector; and
determining the molecular weight and/or molecular weight distribution of the second portion.

25. The method of claim 24 further comprising introducing at least a part of the sample to an additional column selected from the group consisting of a hydrophobic interaction column, an ion exchange column, and a high performance liquid chromatography column.

26. The method of claim 24 further comprising fractionating the second portion of the sample fraction via the rapid gel chromatography element in less than about 10 minutes.

* * * * *